United States Patent [19]
Semple et al.

[11] Patent Number: 5,932,733
[45] Date of Patent: Aug. 3, 1999

[54] 3-AMINO-2-OXO-1-PIPERIDINEACETIC DERIVATIVES CONTAINING AN ARGININE MIMIC AS ENZYME INHIBITORS

[75] Inventors: Joseph E. Semple; Odile E. Levy; Ruth F. Nutt; William C. Ripka, all of San Diego, Calif.

[73] Assignee: Corvas International, Inc., San Diego, Calif.

[21] Appl. No.: 08/482,117

[22] Filed: Jun. 7, 1995

Related U.S. Application Data

[63] Continuation-in-part of application No. 08/261,498, Jun. 17, 1994, abandoned, and application No. 08/356,831, Dec. 13, 1994, abandoned.

[51] Int. Cl.⁶ ........................ A61K 31/445; C07D 211/56
[52] U.S. Cl. ..................... 546/188; 540/463; 540/488; 540/492; 540/527; 544/129; 544/157; 544/159; 544/164; 544/359; 544/360; 546/221; 546/208; 548/119; 548/184; 548/230; 548/321.5; 548/413; 548/550
[58] Field of Search ................. 514/85, 89, 92, 514/94, 212, 218, 227.2, 237.2, 237.5, 247, 316, 327, 376, 386, 422, 424; 540/463, 527; 544/59, 60, 129, 157, 159, 164, 359, 360; 546/188, 189, 208, 209, 210, 221; 548/119, 182, 184, 186, 229, 321.5, 413, 550

[56] References Cited

U.S. PATENT DOCUMENTS

| | | | |
|---|---|---|---|
| 4,399,065 | 8/1983 | Bajusz et al. | 530/331 |
| 4,433,152 | 2/1984 | Muramatsu et al. | 546/193 |
| 5,371,072 | 12/1994 | Webb et al. | 514/18 |
| 5,424,334 | 6/1995 | Abood et al. | 514/562 |
| 5,492,895 | 2/1996 | Vlasuk et al. | 514/18 |

FOREIGN PATENT DOCUMENTS

| | | | |
|---|---|---|---|
| A0 526 877 | 2/1993 | European Pat. Off. | 401/6 |
| A2 490 632 | 3/1982 | France | 103/37 |

OTHER PUBLICATIONS

Skiles, J.W. et al Bioorg. Med. Chem. Lett. 1993, 3(4), 773–778.
Coughlin, P. et al Proc. Natl. Acad. Sci. U.S.A. 1993, 90, 9417–9421.
G. Wagner et al., Pharmazie 39:5, pp. 315–317 (May 1984).
H. Vieweg et al., Pharmazie 42:4, p. 268 (Apr. 1987).
Aldrich Chemical Company, Inc. Catalog (1995) p. 283.
Bachem California Catalog (1993–1994) p. 121.
Bachem Bioscience Catalog (1995) p. 721.
Williams, et al., "1–(((7,7–Dimethyl–2(S)–(2(S)–amino–4–(methylsulfonyl)butyramido)–bicyclo[2,2,1]–heptan–1(S)–yl)methyl)sulfonyl)–4–(2–methylphenyl)piperazine(L–368,889): An Orally Bioavailable, Non–Peptide Oxytocin Antagonist with Potential Utility for Managing Preterm Labor," *J. Med. Chem.*37:565–571 (1994).
Damewood, et al., "Nonpeptidic Inhibitors of Human Leukocyte Elastase. 2. Design, Synthesis, and in vitro Activity of a Series of 3–Amino–6–arylopyridine–2–one Trifluoromethyl Ketones," *J. Med. Chem.*37:3303–3312 (1994).
Skiles, et al., "Elastase Inhibitors Containing Conformationally Restricted Lactams as $P_3$–$P_2$Dipeptide Replacements," *Bioorg. Med. Chem. Lett.*3(4):773–779 (1993).
Freidinger, et al., "Protected Lactam–Bridged Dipeptides for Use as Conformational Constraints in Peptides," *J. Org. Chem.*47:104–109 (1982).

*Primary Examiner*—Alan L. Rotman
*Assistant Examiner*—Garth M. Dahlen
*Attorney, Agent, or Firm*—Lyon & Lyon

[57] ABSTRACT

The present invention discloses peptide aldehydes having a lactam group as part of the peptide backbone and having an original mimic group such as an amidinopiperidine or amidinophengyl tail. These compounds are potent and specific inhibitors of thrombin, their pharmaceutically acceptable salts, pharmaceutically acceptable compositions thereof, and methods of using them as therapeutic agents for disease states in mammals characterized by abnormal thrombosis.

56 Claims, 5 Drawing Sheets

3-AMINO-2-OXO-1-PIPERIDINEACETIC DERIVATIVES CONTAINING AN ARGININE MIMIC AS ENZYME INHIBITORS

CROSS-REFERENCE TO RELATED APPLICATIONS

This application is a Continuation-in-Part of U.S. Ser. No. 08/261,498, filed Jun. 17, 1994, and U.S. Ser. No. 08/356,831, both now abandoned filed Dec. 13, 1994, the disclosures of which are incorporated herein by reference.

TECHNICAL FIELD

In one aspect, the present invention relates compounds which are potent and specific inhibitors of thrombin. In another aspect, the present invention relates to novel peptide aldehydes, their pharmaceutically acceptable salts, and pharmaceutically acceptable compositions thereof which are useful as potent and specific inhibitors of blood coagulation in vitro and in vivo in mammals. In yet another aspect, the invention relates to methods of using these inhibitors as therapeutic agents for disease states in mammals characterized by abnormal thrombosis.

BACKGROUND

Normal hemostasis is the result of a complex balance between the processes of clot formation (blood coagulation) and clot dissolution (fibrinolysis). The complex interactions between blood cells, specific plasma proteins and the vascular surface, maintain the fluidity of blood unless injury and blood loss occur.

Blood coagulation is the culmination of a series of amplified reactions in which several specific zymogens of serine proteases in plasma are activated by limited proteolysis. Nemerson, Y. and Nossel, H. L., Ann. Rev. Med., 33: 479 (1982). This series of reactions results in the formation of an insoluble fibrin matrix which is required for the stabilization of the primary hemostatic plug. The interaction and propagation of the activation reactions occurs through the extrinsic and intrinsic pathways of coagulation.

These pathways are highly inter-dependent and converge in the formation of the serine protease, Factor Xa. Factor Xa catalyzes the penultimate step in the blood coagulation cascade which is the formation of the serine protease thrombin. This step occurs following the assembly of the prothrombinase complex which is composed of factor Xa, the non-enzymatic co-factor Va and the substrate prothrombin assembled on the surface of adhered, activated platelets or systemically circulating membranous microparticles.

Proteolytic activation of zymogen factor X to its catalytically active form, factor Xa, can occur by either the intrinsic or extrinsic coagulation pathways.

The intrinsic pathway is referred to as "intrinsic" because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X which subsequently results in clot formation.

The extrinsic pathway is referred to as "extrinsic" because the tissue factor which binds to and facilitates the activation of factor VII comes from outside the blood. Saito, Id. The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor Xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391(1983). In addition, sequestration of factor Xa in the prothrombinase complex also renders it resistant to inhibition by exogenous heparin therapy which also requires antithrombin III to elicit its anticoagulant effect.

Thrombin is the primary mediator of thrombus formation. Thrombin acts directly to cause formation of insoluble fibrin from circulating fibrinogen. In addition, thrombin activates the zymogen factor XIII to the active transglutaminase factor XIIIa which acts to covalently stabilize the growing thrombus by crosslinking the fibrin strands. Lorand, L. and Konishi, K., Arch. Biochem. Biophys., 105: 58 (1964). Beyond its direct role in the formation and stabilization of fibrin rich clots, the enzyme has been reported to have profound bioregulatory effects on a number of cellular components within the vasculature and blood. Shuman, M. A., Ann. NY Acad. Sci., 405: 349 (1986).

It is believed that thrombin is the most potent agonist of platelet activation, and it has been demonstrated to be the primary pathophysiologic-mediator of platelet-dependent arterial thrombus formation. Edit, J. F. et al., J. Clin. Invest., 84: 18 (1989). Thrombin-mediated platelet activation leads to ligand-induced inter-platelet aggregation principally due to the bivalent interactions between adhesive ligands such as fibrinogen and fibronectin with platelet integrin receptors such as glycoprotein IIb/IIIa which assume their active conformation following thrombin activation. Berndt, M. C. and Phillips, D. R., Platelets in Biology and Pathology, pp 43–74, Elsevier/North Holland Biomedical Press (Gordon, J. L. edit. 1981). Thrombin-activated platelets can also support further thrombin production through the assembly of new prothrombinase and tenase (factor IXa, factor VIIIa and factor X) catalytic complexes on the membrane surface of intact activated platelets and platelet-derived microparticles, following thrombin-mediated activation of the non-enzymatic cofactors V and VIII, respectively. Tans, G. et al., Blood, 77: 2641 (1991). This positive feedback process results in the local generation of large concentrations of thrombin within the vicinity of the thrombus which supports further thrombus growth and extension. Mann, K. G. et al., Blood, 76: 1 (1990).

In contrast to its prothrombotic effects, thrombin has been shown to influence other aspects of hemostasis. These include its effect as an important physiological anticoagulant. The anticoagulant effect of thrombin is expressed following binding of thrombin to the endothelial cell membrane glycoprotein, thrombomodulin. This is thought to result in an alteration of the substrate specificity of thrombin thereby allowing it to recognize and proteolytically activate circulating protein C to give activated protein C (aPC). Musci, G. et al., Biochemistry, 27: 769 (1988). aPC is a serine protease which selectively inactivates the non-enzymatic co-factors Va and VIIIa resulting in a down-regulation of thrombin formation by the prothrombinase and tenase catalytic complexes, respectively. Esmon, C. T., Science, 235: 1348 (1987). The activation of protein C by thrombin in the absence of thrombomodulin is poor.

Thrombin has also been shown to be a potent direct mitogen for a number of cell types, including cells of mesenchymal origin such as vascular smooth muscle cells. Chen, L. B. and Buchanan, J. M., Proc. Natl. Acad. Sci. USA, 72: 131 (1975). The direct interaction of thrombin with vascular smooth muscle also results in vasoconstriction. Walz, D. A. et al., Proc. Soc. Expl. Biol. Med., 180: 518 (1985). Thrombin acts as a direct secretagogue inducing the release of a number of bioactive substances from vascular endothelial cells including tissue plasminogen activator. Levin, E. G. et al., Thromb. Haemost., 56: 115 (1986). In addition to these direct effects on vascular cells, the enzyme can indirectly elaborate potent mitogenic activity on vascular smooth muscle cells by the release of several potent growth factors (e.g. platelet-derived growth factor and epidermal growth factor) from platelet a-granules following thrombin-induced activation. Ross, R., N. Engl. J. Med., 314: 408 (1986).

Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an cute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively. Ross, A. M., Thrombosis in Cardiovascular Disorder, p. 327, W. B. Saunders Co. (Fuster, V. and Verstraete, M. edit. 1991); Califf, R. M. and Willerson, J. T., Id. at p 389. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered i.v., has not been shown to be universally effective in the treatment or prevention of acute arterial thrombosis or rethrombosis. Prins, M. H. and Hirsh, J., J. Am. Coll. Cardiol., 67: 3A (1991).

Besides the unpredictable, recurrent thrombotic reocclusion which commonly occurs following PTCA, a rofound restenosis of the recanalized vessel occurs in 30 to 40% of patients 1 to 6 months following this procedure. Califf, R. M. et al., J. Am. Coll. Cardiol., 17: 2B (1991). These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

The need for safe and effective therapeutic anticoagulants has in one aspect focused on the role of the serine protease thrombin in blood coagulation.

Most preferred natural substrates for thrombin are reported to contain an uncharged amino acid in the P3 recognition subsite. For example, the thrombin cleavage site on the Aα chain of fibrinogen, which is the primary physiological substrate for thrombin, is reported to contain a glycine residue in this position while the cleavage site on the Bβ chain contains a serine, as shown below:

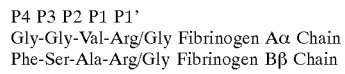

P4 P3 P2 P1 P1'
Gly-Gly-Val-Arg/Gly Fibrinogen Aα Chain
Phe-Ser-Ala-Arg/Gly Fibrinogen Bβ Chain Peptidyl derivatives having an uncharged residue in the P3 position are said to bind to the active site of thrombin and thereby inhibit the conversion of fibrinogen to fibrin and cellular activation have been reported. These derivatives have either an aldehyde, chloromethyl ketone or boronic acid functionality associated with the P1 amino acid. For example, substrate-like peptidyl derivatives such as D-phenylalanyl-prolyl-argininal (D-Phe-Pro-Arg-al), D-phenylalanyl-prolyl-arginine-chloromethyl ketone (P-PACK) and acetyl-D-phenylalanyl-prolyl-boroarginine (Ac-(D-Phe)-Pro-boroArg) have been reported to inhibit thrombin by directly binding to the active site of the enzyme. Bajusz, S., Symposia Biologica Hungarica, 25: 277 (1984), Bajusz, S. et al, J. Med. Chem., 33: 1729 (1990) and Bajusz, S. et al., Int. J. Peptide Protein Res. 12: 217 (1970); Kettner, C. and Shaw, E., Methods Enzymol., 80: 826 (1987), Kettner, C. et al., EP 293,881 (published Dec. 7, 1988), Kettner, C., et al., J. Biol. Chem., 265: 18209 (1990). These molecules have been reported to be potent anticoagulants in the prevention of platelet-rich arterial thrombosis. Kelly, A. B. et al., Thromb. Haemostas., 65: 736 at abstract 257 (1991). Other peptidyl aldehydes have been proposed or reported as inhibitors of thrombin. Bey, P. et al., EP 363,284

(published Apr. 11, 1990) and Balasubramanian, N. et al., EP 526,877 (published Feb. 10, 1993).

Peptidyl compounds which are said to be active site inhibitors of thrombin but which differ in structure from those containing a uncharged amino acid in the P3 recognition subsite have been reported.

The compound, Argatroban (also called 2R,4R-4-methyl-1-[N-2-(3-methyl-1,2,3,4-tetrahydro-8-quinolinesulfonyl)-L-argininal]-2-piperdinecarboxylic acid), is also reported to bind directly to the active site of thrombin and has been thought to be the most potent and selective compound in the class of non-peptidyl inhibitors of this enzyme. Okamoto, S. et al., Biochem. Biophys. Res. Commun., 101: 440 (1981). Argatroban has been reported to be a potent antithrombotic agent in several experimental models of acute arterial thrombosis. Jang, I. K. et al., in both Circulation, 81: 219 (1990) and Circ. Res., 67: 1552 (1990).

Peptidyl compounds which are said to be inhibitors of thrombin and whose mode of action is thought to be by binding to both the active site and another site on the enzyme have been reported. Hirudin and certain peptidyl derivatives of hirudin have been reported to inhibit both conversion of fibrinogen to fibrin and platelet activation by binding to either both the active site and exo site, or the exo site only, of thrombin. Markwardt, F., Thromb. Haemostas., 66: 141 (1991). Hirudin is reported to be a 65 amino acid polypeptide originally isolated from leech salivary gland extracts. It is said to be one of the most potent inhibitors of thrombin known. Marki, W. E. and Wallis, R. B., Thromb. Haemostas., 64: 344 (1990). It has been reported to inhibit thrombin by binding to both its anion-binding exo-site and to its catalytic active site which are distinct and physically distant from each other. Rydel, T. J. et al., Science, 249:277 (1990). Hirudin has been reported to be a potent antithrombotic agent in vivo. Markwardt, F. et al., Pharmazie, 43: 202 (1988); Kelly, A. B. et al., Blood, 77: 1 (1991). In addition to its antithrombotic effects, hirudin has been reported to also effectively inhibit smooth muscle proliferation and the associated restenosis following mechanical damage to a atherosclerotic rabbit femoral artery. Sarembock, I. J. et al., Circulation, 84: 232 (1991).

Hirugen has been reported to be a peptide derived from the anionic carboxy-terminus of hirudin. It is reported to bind only to the anion binding exo-site of thrombin and thereby inhibit the formation of fibrin but not the catalytic turnover of small synthetic substrates which have access to the unblocked active site of the enzyme. Maraganore, J. M. et al., J. Biol. Chem., 264: 8692 (1989); Naski, M. C. et al., J. Biol. Chem., 265: 13484 (1990). The region of hirudin represented by hirugen has been reported, as according to by x-ray crystallographic analysis, to bind directly to the exo site of thrombin. Skrzypczak-Jankun, E. et al., Thromb. Haemostas., 65: 830 at abstract 507 (1991). moreover, the binding of hirugen has also been reported to enhance the catalytic turnover of certain small synthetic substrates by thrombin, indicating that a conformational change in the enzyme active site may accompany occupancy of the exo-site. Liu, L. W. et al., J. Biol. Chem, 266:16977 (1991). Hirugen also is reported to block thrombin-ediated platelet aggregation. Jakubowski, J. A. and Maraganore, J. M., Blood, 75: 399 (1990).

A group of synthetic chimeric molecules comprised of a hirugen-like sequence linked by a glycine-spacer region to the peptide, D-phenylalanyl-prolyl-arginine, which is based on a preferred substrate recognition site for thrombin, has been termed to be hirulog. Maraganore et al., U.S. Pat. No. 5,196,404 (Mar. 23, 1993). The hirugen-like sequence is said to be linked to this peptide through the C-terminal end of the peptide. Maraganone, J. M. et al., Biochemistry, 29: 7095 (1990). The hirulogs have been reported to be an effective antithrombotic agents in preventing both fibrin-rich and platelet-rich thrombosis. Maraganone, J. M. et al., Thromb. Haemostas., 65: 651 at abstract 17 (1991).

Certain benzamidines have been reported to inhibit thrombin though non-selectively. 4-amidinophenylpyruvic acid (APPA) has been reported to be a thrombin inhibitor with low toxicity and favourable pharmacokinetics. However, this compound was reported to be non-selective, inhibiting trypsin, plasmin and kallikrein. Markwardt et al., Thromb. Res., 1:243–52 (1972). Other benzamidine-derived structures which have been reported to inhibit thrombin include the cylic amides of $N^\alpha$-substituted 4-amidinophenylalanine and 2-amino-5-(4-amidinophenyl)-1-valeric acid. The inhibitory constant displayed by these compounds was reported to be in the micromolar range. Markwardt et al., Thromb. Res., 17:425–31 (1980). Moreover, derivatives of 4-amidinophenylalanine whose α-amino group is linked to the arylsulfonyl residue via an ω-aminoalkylcarboxylic acid as spacer have also been assessed for their inhibitory effect. Among these $N^\alpha$-(2-naphthylsulphonylglycyl)-4-amidino-phenylalanine piperidide (α-NAPAP) has been reported to possess an affinity for thrombin ($K_i=6\times10^{-9}$M). Banner et al., J. Biol. Chem., 266:20085 (1991) and Sturzebecher et al., Thromb. Res., 29:635–42 (1983).

Certain bis-benzamidines have been reported to inhibit thrombin. The antithrombin activity of bis-benzamidines was reported to increase with the length and bulkiness of the central chain. However, these compounds were reported to be generally toxic in the micromolar range where they are also inhibitory. Geratz et. al., Thromb. Diath. Haemorrh., 29:154–67 (1973); Geratz et. al., J. Med. Chem., 16:970–5 (1973); Geratz et. al., J. Med. Chem., 19:634–9 (1976); Walsmann et. al., Acta Biol. Med. Germ., 35:K1–8 (1976); and Hauptmann et. al., Acta Biol. Med. Germ., 35:635–44 (1976).

Certain amidino-bearing aromatic ring structures such a beta-naphthamidines have been reported to possess modest antithrombin and anticoagulant activity. This class of compounds include the non-selective 6-amidino-2-naphthyl-4-guanidinobenzoate dimethanesulfonate (FUT 175). Fuji et al., Biochim. Biophys. Acta, 661:342–5 (1981); and Hitomi et. al., Haemostasis, 15:164–8 (1985).

Certain phenylguanidines have been reported to inhibit thrombin. Derivatives of 4-guanidinophenylalanine with inhibitory constants in the micromolar range have been reported to inhibit thrombin. This class includes the $N^\alpha$-tosylated and dansylated 4-guanidino phenylalanine piperidides. Claeson et. al., Thromb. Haemostas., 50:53 (1983). Another compound, [Ethyl p-(6-guanidinohexanoyloxy) benzoate] methane sulfonate (FOY) was reported to be a non-selective competitive inhibitor of thrombin. Ohno et al., Thromb. Res., 19:579–588 (1980).

SUMMARY OF THE INVENTION

The present invention is directed to novel peptide aldehyde compounds having an arginine mimic at $P_1$ and a lactam group as part of the peptide backbone. These compounds are active as selective inhibitors of thrombin.

Novel compounds of the present invention have the following formula:

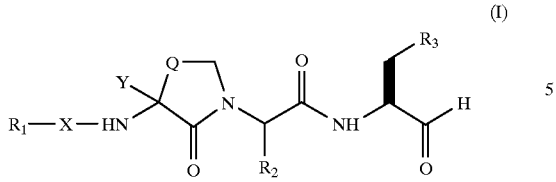

(I)

wherein:
(a) X is selected from the group consisting of —S(O)$_2$—, —N(R')—S(O)$_2$—, —(C=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;
(b) R$_1$ is selected from the group consisting of:
(1) alkyl of 1 to about 12 carbon atoms,
(2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons,
(3) cyclic alkyl of 3 to about 15 carbon atoms, which optionally is substituted in the ring carbons with hydroxyl, amino, guanidino, amidino, or alkoxyl or alkyl each of which is 1 to about 3 carbons,
(4) heterocycloalkyl of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, optionally substituted in the ring carbons with hydroxyl, alkoxyl or alkyl each of which is 1 to about 3 carbons, amino, guanidino, or amidino,
(5) heterocyclo of 4 to about 10 ring atoms with the ring atoms selected from carbon and heteroatoms, wherein the heteroatoms are selected from the group consisting of oxygen, nitrogen, and S(O)$_i$, wherein i is 0, 1, or 2, optionally substituted in the ring carbons with hydroxyl, alkoxyl or alkyl each of which is 1 to about 3 carbons, amino, guanidino, or amidino,
(6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons,
(7) aryl of about 6 to about 14 carbon atoms which is optionally mono-, di- or tri-substituted with Y$_1$, Y$_2$, and/or Y$_3$, respectively,
(8) heteroaryl of 5 to 14 atoms with the ring atoms selected from carbon and heteroatoms, wherein the heteroatoms are selected from oxygen, nitrogen, and S(O)$_i$, wherein i is 0, 1, or 2, optionally mono-, di- or tri-substituted with Y$_1$, Y$_2$, and/or Y$_3$, respectively,
(9) aralkyl of about 7 to about 15 carbon atoms which is optionally mono-, di-, or tri-substituted in the aryl ring with Y$_1$, Y$_2$, and/or Y$_3$, respectively,
(10) heteroaralkyl of 6 to 11 atoms with the ring atoms selected from carbon and heteroatoms, wherein the heteroatoms are selected from oxygen, nitrogen, and S(O)$_i$, wherein i is 0, 1, or 2, optionally mono-, di- or tri-substituted with Y$_1$, Y$_2$, and/or Y$_3$, respectively,
(11) aralkenyl of about 8 to about 15 carbon atoms which is optionally mono-, di-, or tri-substituted in the aryl ring with Y$_1$, Y$_2$, and/or Y$_3$, respectively,
(12) heteroaralkenyl of 7 to 12 atoms with the ring atoms selected from carbon and heteroatoms, wherein the heteroatoms are selected from oxygen, nitrogen, and S(O)$_i$, wherein i is 0–2, optionally mono-, di- or tri-substituted with Y$_1$, Y$_2$, and/or Y$_3$, respectively, (13)

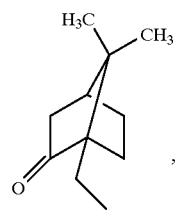

(14)

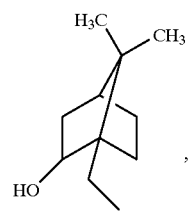

(15)

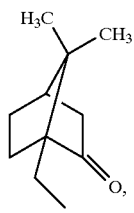

(16)

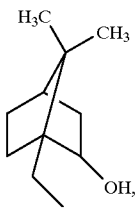

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and (21)

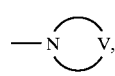

wherein

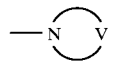

is a 5 to 7 member heterocycle of 3 to 6 ring carbon atoms, where V is —CH$_2$—, —O—, —S(=O)—, —S(O)$_2$— or —S—, wherein Y$_1$, Y$_2$, and Y$_3$ are
(i) independently selected from the group consisting of hydrogen, halogen, cyano, tetrazolyl, amino, guanidino, amidino, methylamino, and methylguanidino, —CF$_3$, —CF$_2$H, —CF$_2$CF$_3$, —CH(CF$_3$)$_2$, —C(OH)(CF$_3$)$_2$, OCF$_3$, OCF$_2$CF$_3$, —OC(O)NH$_2$, —OC(O)NHZ$_1$, —OC(O)NZ$_1$Z$_2$, —NHC(O)Z$_1$, —NHC(O)NH$_2$, —NHC(O)NZ$_1$, —NHC(O)NZ$_1$Z$_2$, —C(O)OH, —C(O)NH$_2$, —C(O)NHZ$_1$, —C(O)OZ$_1$, —P(O)$_3$H, —P(O)$_3$H$_2$, —P(O)$_3$(Z$_1$)$_2$, —S(O)$_3$H, —S(O)$_m$Z$_1$, —Z$_1$, —OZ$_1$, —OH, —NH$_2$, —NHZ$_1$, and —NZ$_1$Z$_2$, wherein m is 0, 1 or 2, and Z$_1$ and Z$_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
(ii) Y$_1$ and Y$_2$ are selected together to be —OC(Z$_3$)(Z$_4$)O, wherein Z$_3$ and Z$_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms,
(c) Q is —(CH$_2$)n—, wherein n is an integer from 1 to 4, or —(CH$_2$)$_q$R$_4$—, wherein q is 1 or 2, and R$_4$ is —S(O)$_p$—, —O—, —N(R$_5$)—, wherein p is 0, 1, or 2 and R$_5$ is selected from the group consisting of hydrogen, alkyl of 1 to 4 carbon atoms, and aryl of 1 to 4 carbon atoms;
(d) R$_2$ is selected from the group consisting of hydrogen, alkyl of 1 to 4 carbon atoms or alkenyl of 2 to 4 carbon atoms; and
(e) R$_3$ is selected from the group consisting of

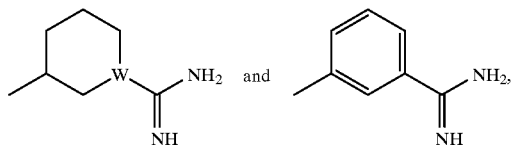

where W is nitrogen or carbon; and
(f) Y is selected from the group of R$_1$ substituents, with the proviso that Y is not

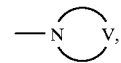

and pharmaceutically acceptable salts thereof.

Among other factors, the present invention is based on our finding that the compounds of our invention are active as potent and selective inhibitors of thrombin. In particular, certain preferred compounds are active as very potent inhibitors of thrombin, yet are significantly less active (on the order of several orders of magnitude) as inhibitors of plasmin and trypsin. This selectivity for inhibition of thrombin gives these compounds a therapeutic advantage in treating or preventing thrombosis in a mammal suspected of having a condition characterized by abnormal thrombosis.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound of the present invention or pharmaceutical composition comprising such a compound.

Definitions

In accordance with the present invention and as used herein, the following terms are defined to have following meanings, unless explicitly stated otherwise:

The term "alkenyl" refers to unsaturated aliphatic groups having at least one double bond.

The term "alkyl" refers to saturated aliphatic groups including straight-chain, branched-chain and cyclic groups.

The terms "alkoxy" and "alkoxyl" refer to a group having the formula, R—O—, wherein R is an alkyl group.

The term "alkoxycarbonyl" refers to —C(O)OR wherein R is alkyl.

The term "aralkenyl" refers to an alkenyl group substituted with an aryl group.

The term "aralkyl" refers to an alkyl group substituted with an aryl group. Suitable aralkyl groups include benzyl, phenethyl, and the like, all of which may be optionally substituted.

The term "aryl" refers to aromatic groups which have at least one ring having a conjugated pi electron system and includes carbocyclic aryl, heterocyclic aryl and biaryl groups, all of which may be optionally substituted.

The term "aryloxy" refers to a group having the formula, R—O—, wherein R is an aryl group.

The term "aralkoxy" refers to a group having the formula, R—O—, wherein R is an aralkyl group.

The term "amino acid" refers to natural amino acids, unnatural amino acids, and amino acid analogs, all in their D and L stereoisomers if their structure allow such stereoisomeric. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically modified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is H or a carbon containing substituent; or (2)

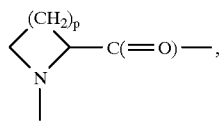

wherein p is 1, 2 or 3 representing the azetidinecarboxylic acid, proline or pipecolic acid residues, respectively.

"Biaryl" refers to phenyl substituted by carbocyclic or heterocyclic aryl as defined herein, ortho, meta or para to the point of attachment of the phenyl ring.

"Brine" refers to an aqueous saturated solution of sodium chloride.

"Carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, difluoromethyl, nitro, and cyano. Substituted naphthyl refers to 1- or 2-naphthyl substituted by lower alkyl, lower alkoxy, or halogen.

"Cycloalkenyl" refers to a cyclic alkenyl group. Suitable cycloalkenyl groups include, for example, cyclopentenyl and cyclohexenyl.

"Cycloalkyl" refers to a cyclic alkyl group. Suitable cycloalkyl groups include, for example, cyclohexyl, cyclopropyl, cyclopentyl, and cycloheptyl.

"Cyclohexylmethyl" refers to a cyclohexyl group attached to $CH_2$.

The term "halogen" refers to fluorine, chlorine, bromine and iodine.

"Heteroaralkenyl" refers to an alkenyl group substitued with a heteroaryl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heteroaralkyl" refers to an alkyl group substituted with a heteroaryl, such as picolyl, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heteroaryl" refers to aryl groups having from 1 to 9 carbon atoms and the remainder of the atoms are heteroatoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroatoms include oxygen, nitrogen, $S(O)_i$, wherein i is 0, 1, or 2, and suitable heterocyclic aryls include furanyl, thienyl, pyridyl, pyrrolyl, pyrimidyl, pyrazinyl, imidazolyl, and the like.

"Heterocyclo" refers to a reduced heterocyclic ring system comprised of carbon, nitrogen, oxygen and/or sulfur atoms, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

"Heterocycloalkyl" refers to an alkyl group substituted with a heterocyclo group, and includes those heterocyclic systems described in "Handbook of Chemistry and Physics", 49th edition, 1968, R. C. Weast, editor; The Chemical Rubber Co., Cleveland, Ohio. See particularly Section C, Rules for Naming Organic Compounds, B. Fundamental Heterocyclic Systems.

The term "lower" referred to herein in connection with organic radicals or compounds defines such with up to and including 5, preferably up to and including 4 and advantageously one or two carbon atoms. Such groups may be straight chain or branched chain.

"Perfluoroalkyl" refers to an alkyl group which has every hydrogen replaced with fluorine.

"Perfluoroaryl" refers to an aryl group which has every hydrogen replaced with fluorine.

"Perfluoroaryl alkyl" refers an aralkyl group in which every hydrogen on the aryl moiety is replaced with fluorine.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

The term "Arg-al" refers to the residue of L-argininal which has the formula:

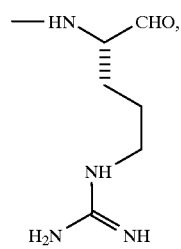

The term "Arg-ol" refers to the residue of L-argininol which has the formula:

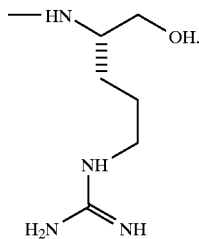

"(S)-N$^g$-nitroargininol hydrochloride" refers to the ompound which has the formula:

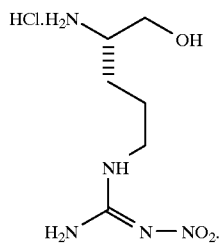

"N-alpha-t-butoxycarbonyl-N$^g$-nitro-L-arginine" refers to the compound which has the formula:

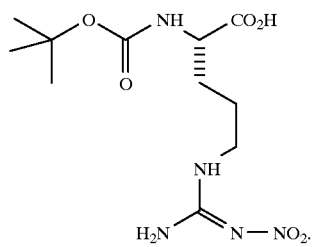

The term "homoAla(cyclo)-Gly" refers to the residue of (S)-3-amino-2-oxo-1-pyrrolidineacetic acid which has the formula:

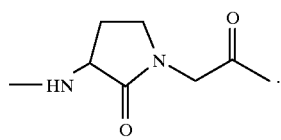

The term "norVal(cyclo)-Gly" refers to the residue of (S)-3-amino-2-oxo-1-piperidineacetic acid which has the formula:

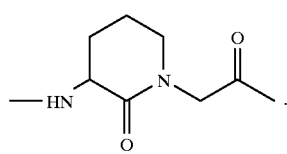

The term "norLeu(cyclo)-Gly" refers to the residue of (R)- or (S)-3-amino-2-oxo-hexahydro-1-azepineacetic acid which has the formula:

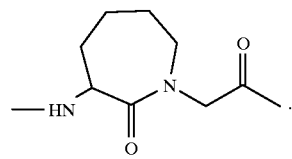

In addition, the following abbreviations stand for the following:

"Bn" refers to benzyl.
"Boc" refers to t-butoxycarbonyl.
"BzlSO$_2$" refers to benzylsulfonyl.
"Cbz" refers to benzyloxycarbonyl.
"DCC" refers to N,N'-dicyclohexylcarbodiimide.
"EDC" refers to 1-ethyl-3-(3-dimethylamino-propyl)carbodiimide hydrochloride salt.
"HBTU" refers to 2-(1H-benzotriazol-1-yl)-1,1,3,3-tetramethyluronium hexafluorophosphate.
"HCl" refers to hydrochloric acid.
"HPLC" refers to high pressure liquid chromatography.
"HOBt" refers to 1-hydroxybenzotriazole monohydrate.
"LiAlH$_4$" refers to lithium aluminum hydride.
"LiAlH$_2$(OEt)$_2$" refers to lithium aluminum dihydride diethoxide.
"THF" refers to tetrahydrofuran.
"TLC" refers to thin layer chromatography.

DETAILED DESCRIPTION OF THE INVENTION

1. Preferred Compounds

Figure 1:
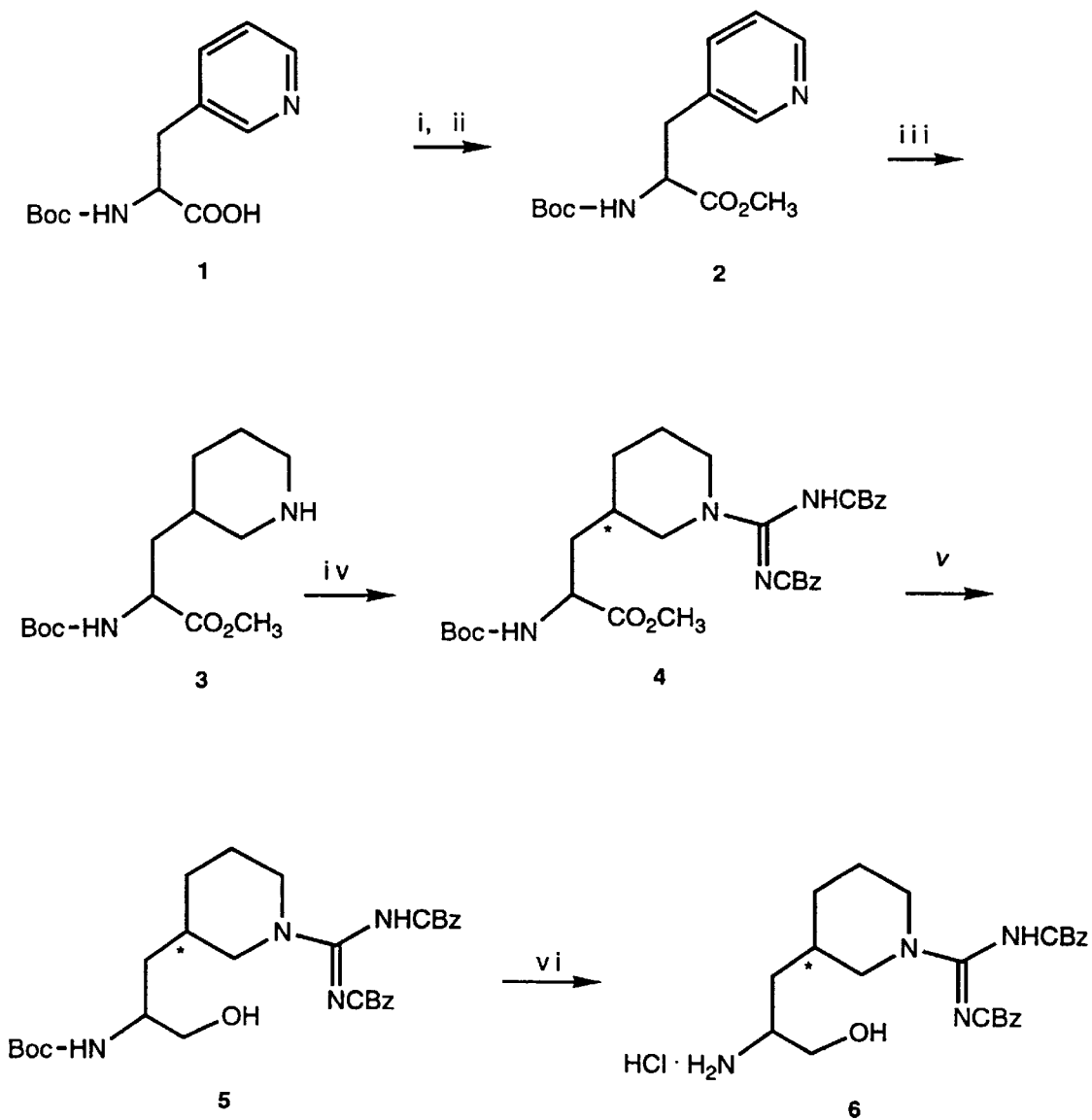
FIG. 1 depicts the reaction scheme for preparation of an intermediate used for the synthesis of the compounds of the present invention. In this figure, "i" through "vi" are defined as: i) thionyl chloride, methanol; ii) di-tert-butyl dicarbonate, pH 7–8; iii) hydrogen gas, platinum oxide in ethanol, water and acetic acid; iv) bis-benzyloxycarbonyl S-methylisothiourea, base, tetrahydrofuran; v) calcium chloride, sodium borohydride in tetrahydrofuran and ethanol; vi) HCl (anhydrous). "*" indicates the position of an asymmetric carbon atom.

Compounds of the present invention have the formula:

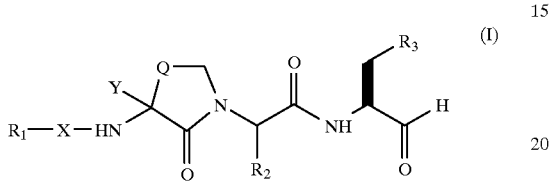

(I)

wherein:

(a) X is selected from the group consisting of —S(O)₂—, —N(R')—S(O)₂—, —(C=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;

(b) $R_1$ is selected from the group consisting of:

(1) alkyl of 1 to about 12 carbon atoms, (2). alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons, (3) cyclic alkyl of 3 to about 15 carbon atoms, which optionally is substituted in the ring carbons with hydroxyl, amino, guanidino, amidino, or alkoxyl or alkyl each of which is 1 to about 3 carbons, (4) heterocycloalkyl of 4 to about 10 ring atoms with the ring atoms selected from carbon and heteroatoms, wherein the heteroatoms are selected from the group consisting of oxygen, nitrogen, and S(O)ᵢ, wherein i is 0, 1, or 2, optionally substituted in the ring carbons with hydroxyl, alkoxyl or alkyl each of which is 1 to about 3 carbons, amino, guanidino, or amidino, (5) heterocyclo of 4 to about 10 ring atoms with the ring atoms selected from carbon and heteroatoms, wherein the heteroatoms are selected from the group consisting of oxygen, nitrogen, and S(O)ᵢ, wherein i is 0, 1, or 2, optionally substituted in the ring carbons with hydroxyl, alkoxyl or alkyl each of which is 1 to about 3 carbons, amino, guanidino, or amidino, (6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons, (7) aryl of about 6 to about 14 carbon atoms which is optionally mono-, di- or tri-substituted with $Y_1$, $Y_2$, and/or $Y_3$, respectively, (8) heteroaryl of 5 to 14 atoms with the ring atoms selected from carbon and heteroatoms, wherein the heteroatoms are selected from oxygen, nitrogen, and S(O)ᵢ, wherein i is 0, 1, or 2, optionally mono-, di- or tri-substituted with $Y_1$, $Y_2$, and/or $Y_3$, respectively, (9) aralkyl of about 7 to about 15 carbon atoms which is optionally mono-, di-, or tri-substituted in the aryl ring with $Y_1$, $Y_2$, and/or $Y_3$, respectively,

(10) heteroaralkyl of 6 to 11 atoms with the ring atoms selected from carbon and heteroatoms, wherein the heteroatoms are selected from oxygen, nitrogen, and S(O)ᵢ, wherein i is 0, 1, or 2, optionally mono-, di- or tri-substituted with $Y_1$, $Y_2$, and/or $Y_3$, respectively,

(11) aralkenyl of about 8 to about 15 carbon atoms which is optionally mono-, di-, or tri-substituted in the aryl ring with $Y_1$, $Y_2$, and/or $Y_3$, respectively,

(12) heteroaralkenyl of 7 to 12 atoms with the ring atoms selected from carbon and heteroatoms, wherein the heteroatoms are selected from oxygen, nitrogen, and S(O)ᵢ, wherein i is 0, 1, or 2, optionally mono-, di- or tri-substituted with $Y_1$, $Y_2$, and/or $Y_3$, respectively, (13)

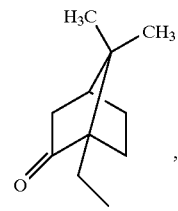

(14)

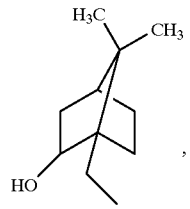

(15)

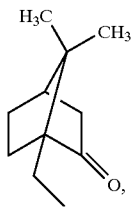

(16)

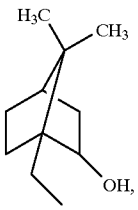

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and
(21)

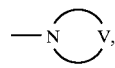

wherein

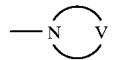

is a 5 to 7 member heterocycle of 3 to 6 ring carbon atoms, where V is —$CH_2$—, —O—, —S(=O)—, —S(O)$_2$— or —S—, wherein $Y_1$, $Y_2$, and Y3 are
(i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)NH_2$, —$C(O)NHZ_1$, —$C(O)OZ_1$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or
(ii) $Y_1$ and $Y_2$ are selected together to be —$OC(Z_3)$ ($Z_4$)O, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms,
(c) Q is —$(CH_2)_n$—, wherein n is an integer from 1 to 4, or —$(CH_2)_qR_4$—, wherein q is 1 or 2, and $R_4$ is —$S(O)_p$—, —O—, —$N(R_5)$—, wherein p is 0, 1, or 2 and $R_5$ is selected from the group consisting of hydrogen, alkyl of 1 to 4 carbon atoms, and aryl of 1 to 4 carbon atoms;
(d) $R_2$ is selected from the group consisting of hydrogen, alkyl of 1 to 4 carbon atoms or alkenyl of 2 to 4 carbon atoms; and
(e) $R_3$ is selected from the group consisting of

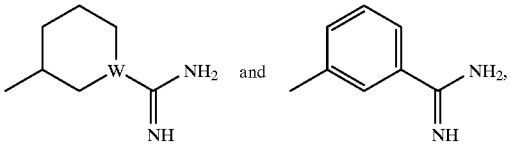

where W is nitrogen or carbon; and
(f) Y is selected from the group of $R_1$ substituents, with the proviso that Y is not

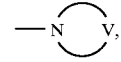

and pharmaceutically acceptable salts thereof.

Preferred X groups include a direct link, —$SO_2$—, —NH——$S(O)_2$—, and —N(R')—$S(O)_2$—. Especially preferred X groups include a direct link and —$SO_2$—.

Preferred $R_1$ groups include alkyl, aralkyl and aryl groups. Suitable aryl groups include substituted or unsubstituted phenyl and naphthyl. Preferred aryl substituents include, —C(O)OH—, —$C(O)OZ_1$—, —$CH_3$, —$OCH_3$—, and —$CF_3$—. Meta and/or ortho substitutions are preferred. Especially preferred $R_1$ groups include aralkyl groups. Particularly preferred $R_1$ groups include substituted or unsubstituted benzyl and phenethyl groups. Cyclohexyl and cyclohexylmethyl are especially preferred $R_1$ groups.

Preferred are compounds where Q is —$(CH_2)_2$— or —$(CH_2)_3$—.

Preferred $R_2$ groups include hydrogen.

Preferred $R_3$ groups include those having a saturated six membered ring. Especially preferred are those $R_3$ groups where W is nitrogen.

Preferred Y groups are selected from the group consisting of
(1) hydrogen,
(2) phenyl-$(CH_2)_x$—, wherein x is an integer from 0 to 3, and the phenyl is optionally mono-, di-, or tri-substituted with with $Y_1$, $Y_2$, and/or $Y_3$, respectively,
(3) heteroaryl-$(CH_2)_x$—, wherein x is an integer from 0 to 3, and the heteroaryl is optionally mono-, di-, or tri-substituted with $Y_1$, $Y_2$, and/or $Y_3$, respectively,
(4) heterocycloalkyl-$(CH_2)_x$—, wherein x is an integer from 0 to 3, and the heterocycloalkyl is optionally substituted with hydroxyl, alkoxyl, or alkyl of 1 to about 3 carbons,
(5) $C_5$ to $C_8$ cycloalkenyl, optionally mono-, di-, or tri-substituted with $Z_5$, $Z_6$, and/or $Z_7$, respectively as defined below, (6) $C_5$ to $C_8$ cycloalkyl, optionally mono- di-, or tri-substituted with with $Z_5$, $Z_6$, and/or $Z_7$, respectively, wherein $Z_5$, $Z_6$, and/or $Z_7$ are independently selected from the group consisting of $R_6$, $OR_6$, and $CO_2R_6$, wherein $R_6$ is selected from the group consisting of hydrogen, methyl, alkyl of 1–3 carbon atoms, More preferred Y groups include aralkyl or cycloalkyl groups. Particularly preferred are substituted or unsubstituted benzyl and 1-naphthylmethyl groups. Preferred aromatic substituents include —C(O)OH, —C(O)OZ$_1$, —CH$_3$, —OCH$_3$, and —CF$_3$. Meta and/or ortho substituents are preferred. Preferred cycloalkyl groups include those containing 5–8 ring carbons. Preferred cycloalkyl substitutents include —C(O)OH, —C(O)OZ$_1$, —CH$_3$, —OCH$_3$.

According to a particularly preferred aspect, provided are compounds of formula I wherein X is —S(O)$_2$—, $R_1$ is substituted or unsubstituted aralkyl, Q is —(CH$_2$)$_2$—, $R_2$ is hydrogen and $R_3$ is a saturated six-membered ring, more preferably a ring wherein W is nitrogen.

A very preferred aspect is directed to such compounds where $R_1$ is substituted or unsubstituted benzyl.

According to another particularly preferred aspect, provided are compounds wherein X is —S(O)$_2$—, $R_1$ is substituted or unsubstituted aralkyl, Q is —(CH$_2$)$_3$—, $R_2$ is hydrogen and $R_3$ is a saturated six-membered ring, more preferably a ring wherein W is nitrogen. A very preferred aspect is directed to such compounds where $R_1$ is substituted or unsubstituted benzyl.

Preferred compounds of this invention include those whose synthesis is described in Examples 12, 20, 31, 37, 41, and 43

Especially preferred compounds of the present invention include:

N-(benzylsulfonyl-norVal(cyclo)-Gly)-3-[3-piperidyl-(N-guanidino)]-L-alaninal (Example 12),
N-(benzylsulfonyl-norLeu(cyclo)-Gly)-3-[3-piperidyl-(N-guanidino)]-L-alaninal (Example 20),
N-(benzylsulfonyl-norVal(cyclo)-Gly-D,L-3-amidinophenylalaninal,
N-(benzylsulfonyl-norLeu(cyclo)-Gly-D,L-3-amidinophenylalaninal (Example31),
N-(norVal(cyclo)-Gly)-3-[3-piperidyl-(N-guanidino)]-L-alaninal,
N-(norLeu(cyclo)-Gly)-3-[3-piperidyl-(N-guanidino)]-L-alaninal,
N-[(S)-3-N-phenylethylamino-2-oxo-1-piperidineacetyl]-3-[3-piperidyl-(N-guanidino)]-L-alaninal,
N-[(S)-3-N-phenylpropylamino-2-oxo-1-piperidineacetyl]-3-[3-piperidyl-(N-guanidino)]-L-alaninal,
N-[(S)-3-N-phenylethylamino-hexahydro-2-oxo-azepine-1-acetyl]-3-[3-piperidyl-(N-guanidino)]-L-alaninal
N-(D, L-a-benzyl-norVal(cyclo)Gly)-3-[3-piperidyl-(N-guanidino)]-L-alaninal,
N-(D, L-a-benzyl-norLeu(cyclo)Gly)-3-[3-piperidyl-(N-guanidino)]-L-alaninal,
N-(1-naphthyl-SO$_2$-norVal(cyclo)-Gly)-3-[3-piperidyl-(N-guanidino)]-L-alaninal (Example 41b),
N-(2-naphthyl-SO$_2$-norVal(cyclo)-Gly)-3-[3-piperidyl-(N-guanidino)]-L-alaninal,
N-(1-naphthylmethyl-SO$_2$-norVal(cyclo)-Gly)-3-[3-piperidyl-(N-guanidino)]-L-alaninal,
N-(2-naphthylmethyl-SO$_2$-norVal(cyclo)-Gly)-3-[3-piperidyl-(N-guanidino)]-L-alaninal,
N-(phenyl-SO$_2$-norLeu(cyclo)Gly)-3-[3-piperidyl-(N-guanidino)]-L-alaninal (Example 37a),
N-(1-naphthyl-SO$_2$-norLeu(cyclo)-Gly)-3-[3-piperidyl-(N-guanidino)]-L-alaninal (Example 37b),
N-(2-naphthyl-SO$_2$-norLeu(cyclo)-Gly)-3-[3-piperidyl-(N-guanidino)]-L-alaninal (Example 37c),
N-(1-naphthylmethyl-SO$_2$-norLeu(cyclo)-Gly)-3-[3-piperidyl-(N-guanidino)]-L-alaninal,
N-(2-naphthylmethyl-SO$_2$-norLeu(cyclo)-Gly)-3-[3-piperidyl-(N-guanidino)]-L-alaninal,
N-(2-carbomethoxyphenyl-SO$_2$-norLeu(cyclo)-Gly)-3-[3-piperidyl-(N-guanidino)]-L-alaninal (Example 37d),
N-(2-carbomethoxybenzyl-SO$_2$-norLeu(cyclo)-Gly)-3-[3-piperidyl-(N-guanidino)]-L-alaninal (Example 37e),
N-(2-trifluoromethylphenyl-SO$_2$-norLeu(cyclo)-Gly)-3-[3-piperidyl-(N-guanidino)]-L-alaninal (Example 37f),
N-(2-trifluoromethylbenzyl-SO$_2$-norLeu(cyclo)-Gly)-3-[3-piperidyl-(N-guanidino)]-L-alaninal (Example 37g),
N-(cyclohexylmethyl-SO$_2$-norLeu(cyclo)-Gly)-3-[3-piperidyl-(N-guanidino)]-L-alaninal (Example 37i),
N-(cyclohexylmethyl-SO$_2$-norVal(cyclo)-Gly)-3-[3-piperidyl-(N-guanidino)]-L-alaninal (Example 41i),
N-(cyclohexylamino-SO$_2$-norLeu(cyclo)-Gly)-3-[3-piperidyl-(N-guanidino)]-L-alaninal (Example 37j),
N-(2-thiophenemethyl-SO$_2$-norLeu(cyclo)-Gly)-3-[3-piperidyl-(N-guanidino)]-L-alaninal (Example 37k),
N-(phenylamino-SO$_2$-norVal(cyclo)-Gly)-D,L-3-amidinophenylalaninal,
N-(phenylamino-SO$_2$-norLeu(cyclo)-Gly)-3-[3-piperidyl-(N-guanidino)]-L-alaninal (Example 37n),
N-(2-carbomethoxyphenylamino-SO$_2$-norLeu(cyclo)-Gly)-D,L-3-amidinophenylalaninal,
N-(3-carbomethoxybenzyl-SO$_2$-norLeu(cyclo)-Gly)-3-[3-piperidyl-(N-guanidino)]-L-alaninal (Example 37o),
N-(3-carbomethoxybenzyl-SO$_2$-norVal(cyclo)-Gly)-3-[3-piperidyl-(N-guanidino)]-L-alaninal (Example 41o),
N-(3-trifluoromethylbenzyl-SO$_2$-norVal(cyclo)-Gly)-3-[3-piperidyl-(N-guanidino)]-L-alaninal,
N-(3-trifluoromethylbenzyl-SO$_2$-norLeu(cyclo)-Gly)-3-[3-piperidyl-(N-guanidino)]-L-alaninal (Example 37p),
N-(2-methylbenzyl-SO$_2$-norLeu(cyclo)-Gly)-D, L-3-amidinophenylalaninal,
N-(2-methylbenzyl-SO$_2$-norLeu(cyclo)-Gly)-3-[3-piperidyl-(N-guanidino)]-L-alaninal (Example 37q),
N-(3-methylbenzyl-SO$_2$-norLeu(cyclo)-Gly)-3-[3-piperidyl-(N-guanidino)]-L-alaninal (Example 37r),
N-(3-methylbenzyl-SO$_2$-norVal(cyclo)-Gly)-3-[3-piperidyl-(N-guanidino)]-L-alaninal (Example 41r),
N-(3-methoxybenzyl-SO$_2$-norLeu(cyclo)-Gly)-3-[3-piperidyl-(N-guanidino)]-L-alaninal (Example 37t),
N-(3-methoxybenzyl-SO$_2$-norVal(cyclo)-Gly)-3-[3-piperidyl-(N-guanidino)]-L-alaninal (Example 41t),
N-(3-methoxybenzyl-SO$_2$-norVal(cyclo)-Gly)-D, L-3-amidinophenylalaninal,
N-(2-chlorobenzyl-SO$_2$-norLeu(cyclo)-Gly)-3-[3-piperidyl-(N-guanidino)]-L-alaninal (Example 37u),
N-(3-chlorobenzyl-SO$_2$-norLeu(cyclo)-Gly)-3-[3-piperidyl-(N-guanidino)]-L-alaninal (Example 37v),
N-(3-chlorobenzyl-SO$_2$-norVal(cyclo)-Gly)-D, L-3-amidinophenylalaninal,
N-(2-methyl-5-fluorobenzyl-SO$_2$-norLeu(cyclo)-Gly)-3-[3-piperidyl-(N-guanidino)]-L-alaninal (Example 37w),
N-(2-methyl-5-fluorobenzyl-SO$_2$-norLeu(cyclo)-Gly)-D, L-3-amidinophenylalaninal,
N-(2-methyl-5-fluorobenzyl-SO$_2$-norVal(cyclo)-Gly)-3-[3-piperidyl-(N-guanidino)]-L-alaninal (Example 41w),
N-(2-methyl-5-methoxybenzyl-SO$_2$-norLeu(cyclo)-Gly)-3-[3-piperidyl-(N-guanidino)]-L-alaninal (Example 37x),
N-(2-methyl-5-methoxybenzyl-SO$_2$-norLeu(cyclo)-Gly)-D, L-3-amidinophenylalaninal,
N-(Benzyl-PO-(OEt)-norLeu(cyclo)-Gly)-3-[3-piperidyl-(N-guanidino)]-L-alaninal (Example 43a), N-(Benzyl-PO-(Me)-norLeu(cyclo)-Gly)-3-[3-piperidyl-(N-guanidino)]-L-alaninal (Example 43b),
N-(Benzyl-PO-(NHMe)-norLeu(cyclo)-Gly)-3-[3-piperidyl-(N-guanidino)]-L-alaninal (Example 43c),
N-(Benzyl-PO-(OEt)-norLeu(cyclo)-Gly)-D, L-3-amidinophenylalaninal,
N-(Benzyl-PO-(Me)-norVal(cyclo)-Gly)-3-[3-piperidyl-(N-guanidino)]-L-alaninal,
N-(Benzyl-PO-(NHMe)-norVal(cyclo)-Gly)-D,L-3-amidinophenylalaninal,
N-(Benzyl-$SO_2$-homoala(cyclo)-Gly)-3-[3-piperidyl-(N-guanidino)]-L-alaninal (Example 35), and
N-(Benzyl-$SO_2$-homoala(cyclo)-Gly)-D,L-3-amidinophenylalaninal.

According to another aspect, the present invention is directed to salts of the compounds of formula (I). "Salt" includes within its definition, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of trifluoroacetic acid, hydrochloric acid, hydrobromic acid, acetic acid, benzene sulfonic acid and other suitable acid addition salts.

In formula I, carbon atoms bearing the $R_2$ and Y groups are capable of forming stereoisomers. This invention contemplates both stereoisomeric forms.

2. Preparation of Preferred Compounds

The present invention embodies classes of serine protease inhibitors having a five, six, or seven-membered ring in the P3 position. Certain preferred compounds from each of these classes are desribed in the Examples. Examples 32 through 35 present the synthesis of one five-membered compound according to this invention. Examples 1 through 12 and 38 through 41 describe methods of synthesizing a series of six-membered ring compounds within the present invention. Seven-membered ring compounds are synthesized according to the protocols presented in Examples 13 through 31, Examples 36 and 37, and Examples 42 and 43. It will be understood that variations of the Examples can be performed to yield five-, six-, and seven-membered ring compounds similar to those compounds described in the Examples.

Certain intermediates of the present invention are used for the preparation of the compounds of the present invention. For example, 3-[3-piperidyl-(N-guanidino(bis-benzyloxycarbonyl))]-L-alaninol, hydrochloride salt, of Example 5, (S)-3-[(tert-butoxycarbonyl)amino]-2-oxo-1-piperidineacetic acid of Example 6 and (S)-3-benzylsulfonamido-2-oxo-1-azepineacetic acid of Example 17 are made and coupled to provide certain compounds of the present invention.

FIG. 1 exemplifies a preferred reaction scheme for preparation of one preferred intermediate, 6, used in the preparation of the compounds of the present invention. Examples 1 through 5 provides the details of the preferred scheme. As shown in FIG. 1, 6 is prepared in stepwise fashion beginning with N-(t-butoxycarbonyl)-3-(3-pyridyl)alanine, 1 as described below.

1 is esterified with loss of the Boc group, which is then reintroduced to yield an ester, 2. Preferred methods of esterification employ conditions allowing esterification by use of reagents, such as hydrogen chloride or thionyl chloride with an alcohol or diazomethane. Especially preferred methods of esterification include the use of thionyl chloride and alcohols Preferred alcohols include methanol ethanol, propanol, isopropanol or butanol. Especially preferred alcohols include methyl alcohol. Preferred reagents for reintroduction of the Boc group onto the N-alpha nitrogen of 1 include di-t-butyldicarbonate.

2 is hydrogenated to convert its aromatic ring to a saturated ring to give 3. Preferred methods of hydrogenation include those using hydrogen gas and a catalyst. Preferred catalysts include platinum oxide, rhodium on aluminum and rhodium on carbon. Especially preferred catalysts include platinum oxide.

3 is treated so as to introduce a protected guanidino group to give 4. Preferred methods of introducing a protected guanidino groups would include the reaction of amino group of 3 with bis protected S-methylisothiourea.

4 is reduced to convert its ester group to an alcohol group to give to 5. Preferred methods of reducing ester groups to alcohol groups include the use of reducing agents such as calcium borohydride, lithium borohydride, sodium borohydride, lithium aluminum hydride or sodium metal in ethanol. Especially preferred methods of reduction include the use of calcium borohydride or lithium borohydride.

5 is treated to convert its Boc-protected amino group to a free N-alpha amino group to give 6. Preferred methods of removing the Boc group include treatment of 5 with HCl in alcohol, trifluoroacetic acid in a chlorinated hydrocarbon solvent, HCl in acetic acid, HCl in ethereal solvents, HCl in ethyl acetate or methyl acetate, p-toluenesulfonic acid in toluene. Especially preferred methods include treatment of 5 with anhydous HCl in ethyl acetate at 15–30° C., more preferably at 20–25° C.

Figure 2:
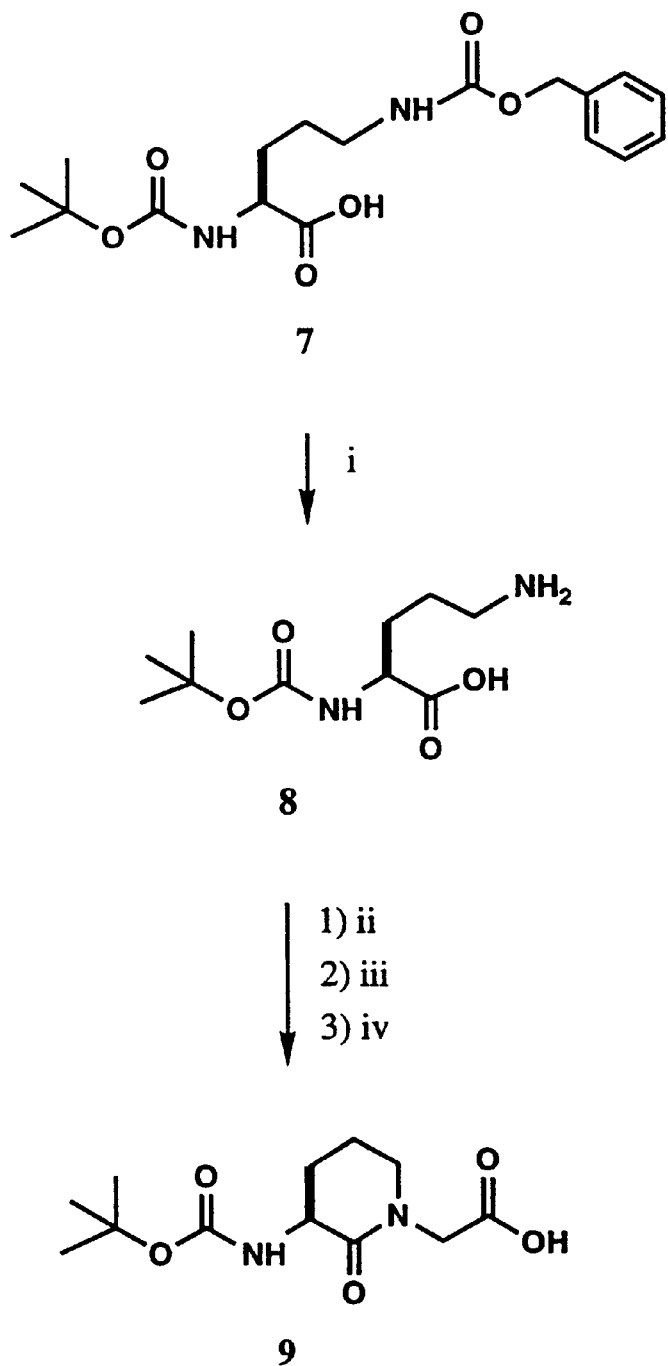
FIG. 2 depicts the reaction scheme for preparation of an intermediate used for the synthesis of the compounds of the present invention. In this figure, "i" through "iv" are defined as: i) hydrogen gas, 10% palladium on carbon; ii) glyoxylic acid; iii) hydrogen gas, 10% palladium on carbon; and iv) 50–60° C.

FIG. 2 exemplifies a preferred reaction scheme for the preparation of another preferred intermediate 9 used in the preparation of the compounds of the present invention. Example 6 provides the details of the preferred scheme.

As shown in FIG. 2, N-alpha-Boc-N-delta-benzyloxycarbonyl-L-ornithine 7 is hydrogenated with hydrogen gas and palladium on carbon to give 8, which is then reacted with glyoxylic acid, hydrogenated with hydrogen gas and palladium on carbon, and heated at an elevated temperature to give 9.

Figure 3:
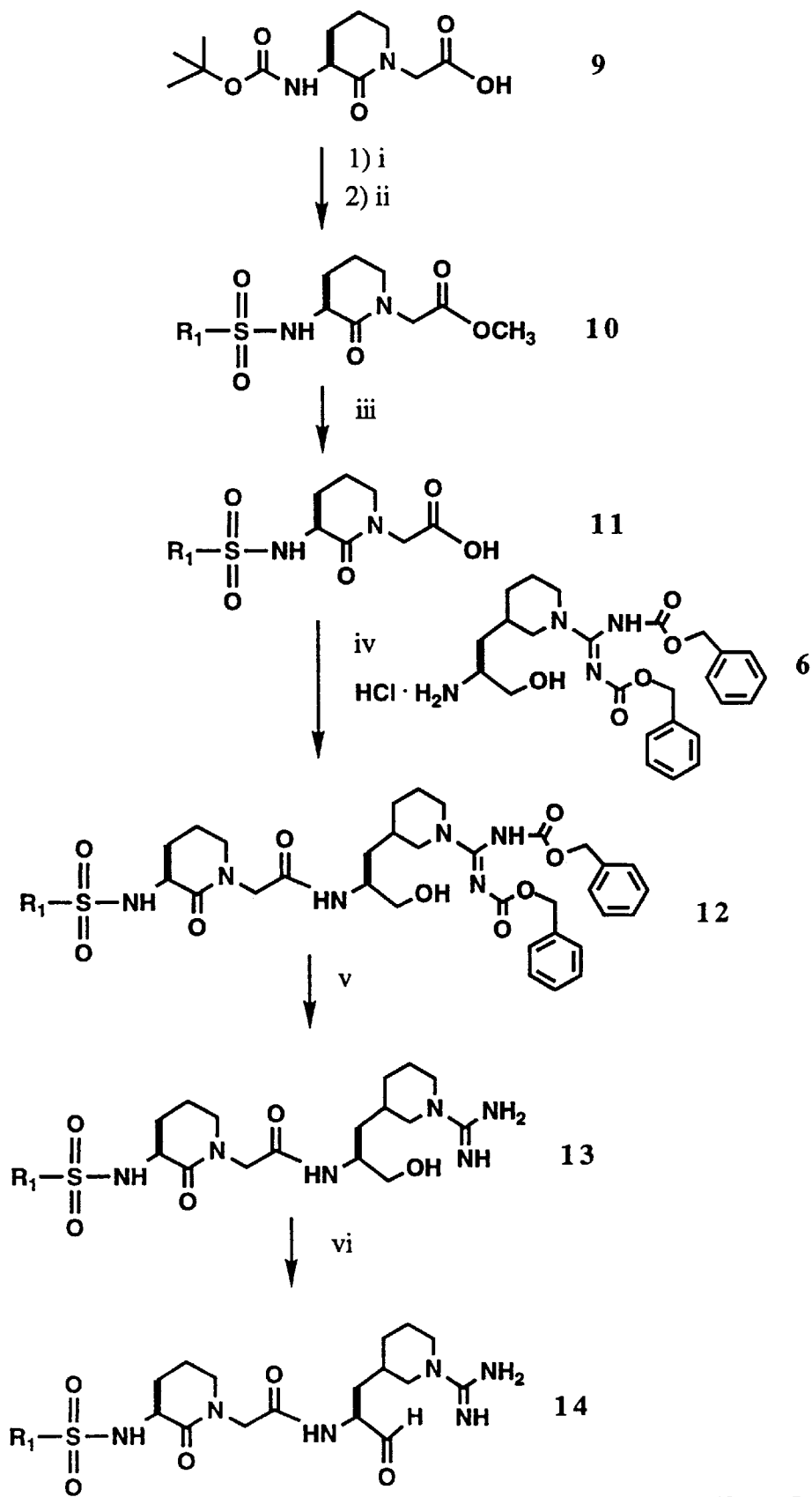
FIG. 3 depicts a preferred reaction scheme for a synthesis of certain compounds of the present invention. In this figure, "i" through "vi" are defined as: i) HCl in methanol; ii) triethylamine, R$_1$—SO$_2$Cl wherein R$_1$ is as defined herein; iii) lithium hydroxide; iv) HOBt, EDC, dimethylaminopyridine, triethylamine; v) hydrogen gas, 10% palladium on carbon; and vi) dimethylsulfoxide, toluene, dichloroacetic acid and EDC.

The compounds of the present invention may be prepared by the preferred reaction schemes depicted in FIG. 3. Examples 7 through 12 provide the details of a preferred scheme for synthesizing compounds according to this invention, including the exemplary compound wherein $R_1$ is benzene.

For example, as shown in FIG. 3, treatment of 9 with saturated HCl in an alcohol cleaves the Boc group and simultaneously esterifies the carboxy group. The free amino group is then reacted with a sulfonyl chloride, depicted by $R_1$—$S(O)_2$—Cl, in the presence of a base to give 10. $R_1$ is as defined herein. 10 is hydrolysed with base to give carboxylic acid. Acid derivative 11 is coupled to 6 (prepared as described in Examples 1 through 5) by carbodiimide coupling to give 12. 12 is hydrogenated with hydrogen gas and palladium on carbon to give 13. 13 is oxidized using dimethylsulfoxide, dichloroacetic acid, toluene and EDC to give 14. 13 may also be oxidized to 14 using pyridine trioxide, triethylamine and dimethylsulfoxide.

The preferred means of chemically coupling (as for example, 11 to 6 of FIG. 3) include formation of a peptide bond by using conventional coupling reagents known in the art. See Bodanszky, N., Peptide Chemistry, pp. 55–73, Springer-Verlag, N.Y. (1988) and references cited therein. The chemical coupling may be either by means of one-step or two-step coupling. In one-step coupling, the two coupling partners are coupled directly. Preferred coupling reagents for one-step coupling of the include DCC with HOBt, EDC with HOBt, HBTU, TBTU, HBTU with HOBt, and TBTU with HOBt. In two-step coupling, an activated ester or anhydride of the C-terminal carboxy group of one coupling partner is formed prior to its coupling to the other coupling partner.

Figure 5:
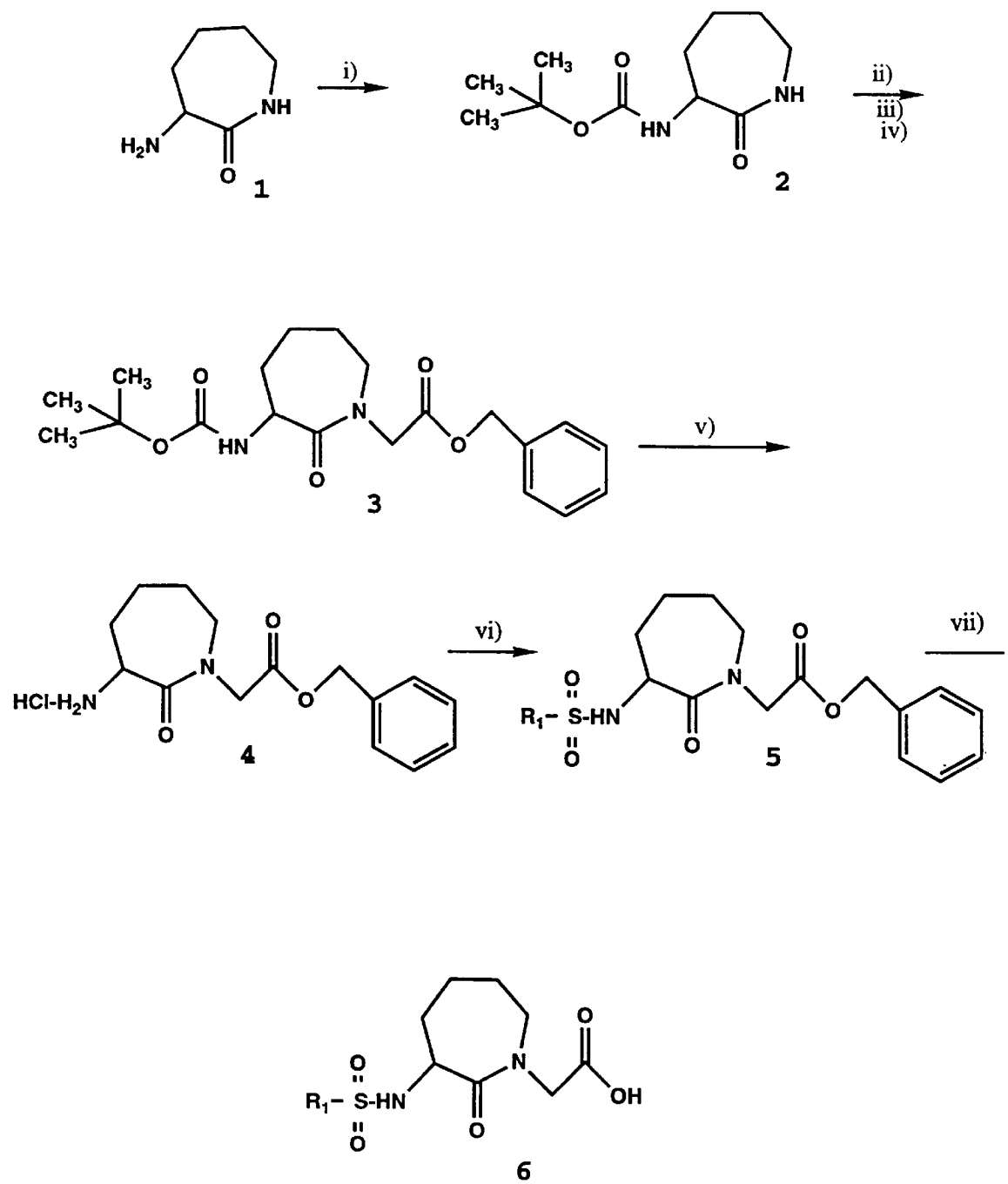
FIG. 5 depicts a preferred reaction scheme for the preparation of certain intermediate compounds useful to synthesize seven membered rings of the present invention. In this figure, i)-vii) are defined as: i) di-t-butyl dicarbonate, sodium bicarbonate in tetrahydrofuran and water; ii) lithium bis(trimethylsilyl)amide and tetrahydrofuran; iii) benzyl bromoacetate; iv) ammonium chloride; v) HCl and ethyl acetate; vi) triethylamine, acetonitrile and R₁—SO₂—Cl, where R₁ is as defined herein; and vii) hydrogen, palladium on carbon and ethanol. Compound 6 from FIG. 5 is treated in an analogous fashion as compound 11 in FIG. 3, to produce the corresponding seven-membered lactam analogs.

Another preferred method for the synthesis of the compounds of the present invention is outlined in FIG. 5. In step i), commercially available 2-Aminocaprolactam 1 is reacted with di-tert-butyldicarbonate in an aqueous THF solution containing a base such as sodium bicarbonate to afford the protected lactam derivative 2. In steps ii) through iv), compound 2 is treated with lithium bis(trimethylsilyl)amide in an inert ethereal solvent such as THF, reacted with benzyl bromoacetate at about 0° to 40°, and then the reaction is quenched with saturated ammonium chloride solution to provide the alkylated intermediate 3. In step v), the amino protecting group of compound 3 is deblocked with a solution of 5N HCl in ethyl acetate and affords the amine hydrochloride salt 4. In step vi), intermediate 4 is coupled with an appropriate sulfonyl chloride of general formula $R_1SO_2Cl$, in an inert solvent such as THF, diethyl ether, dioxane, N,N-dimethyl-formamide, or acetonitrile preferably in the presence of a base such as pyridine, collidine, triethylamine, N-methylmorpholine, or N,N-diisopropylethylamine at about 0° to 40°, preferably between 0° to 25° to afford the sulfonamide derivative 5. In step vii), compound 5 is catalytically debenzylated with hydrogen gas in a suitable solvent like methanol or ethanol using a catalyst such as palladium on charcoal and gives the carboxylic acid 6. The preceding steps may be found in examples 13 through 17 which describes the preparation of the intermediate 6 where R1 is hydrogen. Compound 6 of FIG. 5 may then be coupled with intermediate alcohol derivative 6 found in FIG. 3 and elaborated in an analogous fashion to afford the 7-membered analogs of formula 14 found in FIG. 3. The preceding steps may be found in examples 18 through 20 which describes the preparation of the 7-membered lactam analog wherein R1 is hydrogen. Examples 36–37 and 38–41 teach general methods for the preparation of preferred 7-membered lactam aldehydes and 6-membered lactam aldehydes, respectively.

For compounds of the present invention containing alkenyl or aryl moieties substituted with halogen, cyano, nitro, or —S—$Z_1$, it is preferred to avoid the use of hydrogen gas with palladium on carbon. Instead, it is preferred to use boron tris(trifluoroacetate), $B(OCOCF_3)_3$, to cleave the $N^g$-nitro of the arginine group. The reagent is prepared by the reaction of $BBr_3$ and $CF_3COOH$ in dichloromethane at 0° C. The reagent is also commercially available. Generally, the $N^g$-nitro compound is treated with boron tris (trifluoroacetate) in trifluoroacetic acid at 0° C. Fieser, M. and Fieser, L. F., *Reagents for Organic Synthesis*, p. 46, John Wiley & Sons, New York (1974); Pless, J., and Bauer, W. *Angew. Chem., Internat. Ed.*, 12, 147 (1973).

In addition, another preferred reagent for selective nitro group cleavage is titanium trichloride. This reagent is commercially available. The $N^g$ nitro compound is treated with titanium trichloride in aqueous methanol containing an ammonium acetate buffer followed by exposure of the reaction mixture to air or dimethyl sulfoxide. Freidinger, R. M., Hirschmann, R., and Veber, D. F., *J. Org. Chem.*, 43, 4800 (1978).

3. Selection of Preferred Compound.

The compounds of the present invention are screened for their ability to inhibit thrombin, plasmin, tissue plasminogen activator (t-PA), activated protein C (aPC), chymotrypsin, and trypsin as set forth below. Certain of the preferred compounds are distinguished by their ability to inhibit thrombin, while not substantially inhibiting plasmin, t-PA, aPC, chymotrypsin, and trypsin. With respect to thrombin and the other enzymes and as used herein, the term "not substantially inhibiting" means that the $IC_{50}$ (or $K_i$) for plasmin, t-PA, aPC, chymotrypsin, and trypsin for a given compound is greater than or equal to its $IC_{50}$ (or $K_i$, respectively) for thrombin.

The compounds of the present invention are dissolved in buffer to give solutions containing concentrations such that assay concentrations range from 0 to 100 micromolar. In the assays for thrombin, plasmin, t-PA, aPC, chymotrypsin, and trypsin, a chromogenic synthetic substrate is added to a solution containing test compound and the enzyme of interest and the residual catalytic activity of that enzyme is determined spectrophometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. $K_i$ is that concentration of test compound giving 50% inhibition of the rate of substrate turnover. Examples A and B provide an exemplar of the in vitro assays used to select the compounds of the present invention.

Certain of the preferred compounds of the present invention have a $K_i$ of about 0.001 to about 200 nM in the thrombin assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for plasmin, t-PA, aPC, chymotrypsin, and trypsin which is at least 10 times greater than its $IC_{50}$ for thrombin. Especially preferred compounds have an $IC_{50}$ for plasmin, t-PA, aPC, chymotrypsin, and trypsin which is about 20 to about 100,000 times greater than its $IC_{50}$ for thrombin. More especially preferred compounds have an $IC_{50}$ for plasmin, t-PA, aPC, chymotrypsin, and trypsin which is about 100 to about 1,000,000 times greater than its $IC_{50}$ for thrombin. In the event that a compound of the present invention has an $IC_{50}$ with respect to plasmin, t-PA, aPC, chymotrypsin, or trypsin which is greater than the highest concentration of compound tested, the $IC_{50}$ is taken to be that highest concentration of compound.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The "therapeutically effective amount" of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in *Remington's Pharmeceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixers for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutcial compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

5. Utility and Method.

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vaccum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as a pharmaceutical agent for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired affects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical composition of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1
Preparation of N-(t-butoxycarbonyl)-3-(3-pyridyl)-L-alanine methyl ester

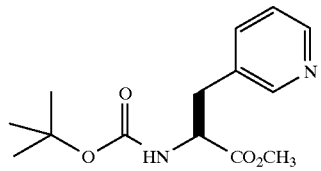

To a solution of N-(t-butoxycarbonyl)-3-(3-pyridyl) alanine (5.0 g, 18.8 mmole) in methanol (100 mL) was added thionyl chloride (2M solution in dichloromethane, 66 mL, 132 mmole) and the solution was stirred overnight at ambient temperature. The methanol was removed under reduced pressure to a minimum volume and ethyl acetate (100 mL) was added. The resulting white precipitate was collected on a glass funnel. To a solution of the collected precipitate in a mixture of tetrahydrofuran/water (40 mL each) was added di-tert-butyl dicarbonate (4.8 g, 21.99 mmole) and sodium carbonate (1.95 g, 18.4 mmole). After stirring for 12 hours at ambient temperature, the reaction mixture was diluted with ethyl acetate (40 mL) and washed with a solution of saturated sodium bicarbonate (25 mL). The organic layer was dried over anhydrous sodium sulfate and concentrated under vacuum to give crude product. This was subjected to flash column chromatography on silica gel (230–400 mesh) column (8×52 cm), eluting with a 10:90 mixture of ethyl acetate/hexane followed by a 60:40 mixture of ethyl acetate/hexane. 4 g (74%) of the title compound was obtained as an oil. Thin-layer chromatography gave an Rf=0.68 (silica gel; ethyl acetate).

Example 2
Preparation of N-(t-butoxycarbonyl)-3-(3-piperidyl)-L-alanine methyl ester, acetate salt

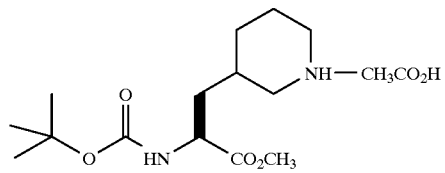

A solution of the compound of Example 1 (5 g, 17.8 mmole) in ethanol (24 mL), acetic acid (6 mL) and water (6 mL) was hydrogenated over platinum oxide (500 mg) at 45 psi for three hours. The catalyst was filtered off and the filtrate concentrated under vacuum to an oily residue (6.89 g) which was taken to the next step without further purification. Thin-layer chromatography in a yielded two spots corresponding to two diastereomers with $R_f$ values of 0.16 and 0.26, respectively (silica gel; 4:1:1 n-butanol/acetic acid/water).

Example 3
Preparation of N-(t-butoxycarbonyl)-3-[3-piperidyl-(N-guanidino (bis-benzyloxycarbonyl))]-L-alanine methyl ester

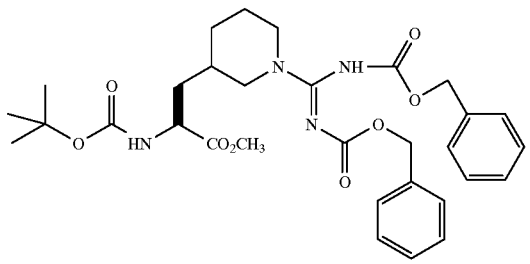

To a solution of the compound of Example 2 (6.89 g, 19.9 mmole) in tetrahydrofuran (80 mL) was added the S-methylisothiourea bis-benzyloxycarbonyl (7.13 g, 19.9 mmole) followed by N-methylmorpholine (4.37 mL), and the reaction was stirred at ambient temperature for 18 hours. The reaction mixture was concentrated under vacuum and the resulting residue was picked-up in ethyl acetate (100 mL) and washed with 1N sodium bisulfate and saturated sodium chloride (50 mL each). After drying over anhydrous sodium sulfate, the solvents were removed under vacuum and the crude title compound was subjected to flash column chromatography on silica gel (230–400 mesh) column (5.5× 45 cm) eluting with 1:9 ethyl acetate/hexanes (two column volumes), followed by 1:1 ethyl acetate/hexanes. 2.75 g the title compound was obtained as a mixture of two diastereomers. Thin-layer chromatography gave two spots with $R_f$ values of 0.57 and 0.62, respectively (silica gel; 1:1 ethyl acetate/hexanes).

Example 4
Preparation of N-(t-butoxycarbonyl)-3-[3-piperidyl-(N-guanidino (bis-benzyloxycarbonyl))]-L-alaninol

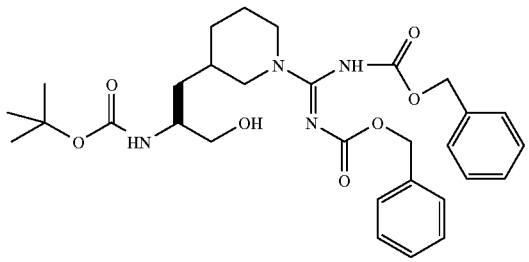

To a stirred solution of the compound of Example 3 (2.23 g, 3.7 mmole) in absolute ethanol (8 mL) and anhydrous tetrahydrofuran (4 mL) was added calcium chloride (844 mg, 7.6 mmole) and sodium borohydride (575 mg, 15.2 mmole). After 12 hours at ambient temperature, the reaction mixture was concentrated under vacuum and the resulting residue was partitioned between ethyl acetate and 1N sodium bisulfate (10 mL each). After separating the two layers, the organic layer was washed twice more with 1N sodium bisulfate, dried over anhydrous sodium sulfate and concentrated under vacuum gave a residue. Flash column chromatography of the residue on silica gel (230–400 mesh) column (8×52 cm) eluting with ethyl acetate affords 1.3 g of the title compound as a white foam. Thin layer chromatography yielded two spots corresponding to two diastereomers with $R_f$ values of 0.18 and 0.27, respectively (silica gel; 1:1 ethyl acetate/hexanes).

Example 5

Preparation of 3-[3-piperidyl-(N-guanidino(bis-benzyloxycarbonyl))]-L-alaninol, hydrochloride salt

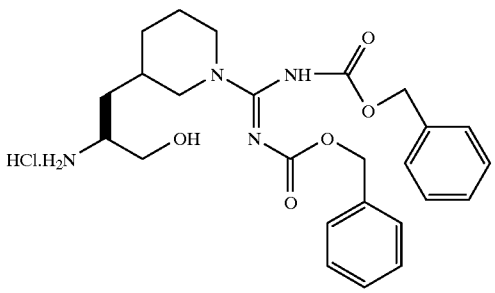

The compound of Example 4 (290 mg, 0.57 mmole) was treated with 2.5N anhydrous hydrochloric acid in ethyl acetate (2.0 mL) at ambient temperature for one hour. The solvent was removed under vacuum to a sticky-white solid (260 mg). This was taken to the next step without further purification. $^1$H NMR spectrum taken in CD$_3$OD showed no butoxycarbonyl protons at 1.4 ppm.

Example 6

Preparation of (S)-3-[(tert-butoxycarbonyl)amino]-2-oxo-1-piperidineacetic acid

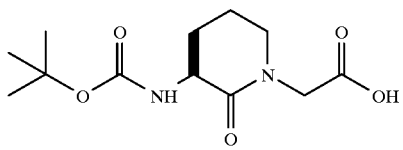

This compound was made in 4 steps by a modification of the literature procedure of D. F. Veber and R. M. Freidinger, U.S. Pat. No. 4,192,875 (Mar. 11, 1980); and R. M. Freidinger, et. al, J. Org. Chem., 47:104–109 (1982). The new method disclosed below proceeds through cleaner intermediates and thus allows for the preparation of large quantitites of material in a high state of purity.

N-alpha-Boc-N-delta-benzyloxycarbonyl-L-ornithine (100.3 g, 0.27 mole) was dissolved in a solution of methanol (450 mL), water (320 mL) and acetic acid (46.5 mL). 10% palladium on carbon catalyst (10.0 g) was added and the mixture was hydrogenated on a Parr apparatus at 35 psi for 2.5 hours. Thin-layer chromatography (silica gel; 20:10:3 dichloromethane/methanol/acetic acid; ninhydrin) showed clean conversion to N-alpha-Boc-L-ornithine.

After purging with nitrogen, glyoxylic acid (27.72 g, 0.30 mole) was added, the mixture was stirred at ambient temperature for 50 hours, hydrogenated at 35 psi for 17 hours, and the catalyst was filtered off. A fresh portion of 10% palladium on carbon catalyst (5 g) was added and the mixture was hydrogenated for a further 20 hours on the Parr Shaker at 40 psi. The catalyst was removed by filtration and the filtrate was concentrated to dryness under vacuum. The residue was taken up in methanol and reevaporated. This process was repeated and the residue was pumped at <1 mm Hg overnight to afford a yellow foam.

The crude intermediate was dissolved in dry dimethylformamide (625 mL) and heated to 50–60° C. for 2.5 hours. The solvent was removed under vacuum at 80° C. The resultant oil was dissolved in 500 mL of dichloromethane and extracted with 500 mL of 1M sodium hydroxide solution. The aqueous solution was extracted with 500 mL of dichloromethane, acidified with cooling with 550 mL of 1M HCl, re-extracted with 5×500 mL dichloromethane and 2×500 mL 9:1 dichloromethane/isopropanol. The combined organic layers were dried over anhydrous magnesium sulfate and evaporated to afford 50 g (67% yield) of the title compound as a solidifying oil, judged pure (single spot with Rf=0.30) by thin-layer chromatography (silica gel; 27:3:1 dichloromethane/methanol/acetic acid).

Example 7

Preparation of norVal(cyclo)-Gly-O-methyl ester, hydrochloride salt

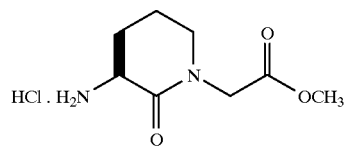

The compound of Example 6 (43.5 g, 0.160 mole) was dissolved in 150 mL of absolute methanol, cooled to 0° C., and treated dropwise with saturated HCl in methanol (400 mL). The solution was stirred at 0° C. for 1 hour and then warmed to ambient temperature and stirred for 14 hours. The solution was concentrated under vacuum to afford the title compound as a clear oil which was used directly in the next example. Thin-layer chromatography gave an Rf=0.25 (silica gel; 27:3:1 dichloromethane/methanol/concentrated ammonium hydroxide).

Example 8

Preparation of N-benzylsulfonyl-norVal(cyclo)-Gly-O-methyl ester

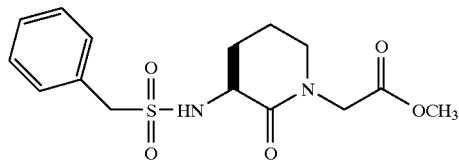

The compound of Example 7 (19.1 g, 85.8 mmole) was slurried in 850 mL of dry acetonitrile and was treated with benzylsulfonyl chloride (32.7 g, 0.172 mole). The solution was cooled to 0° C. and treated dropwise with triethylamine (60.0 mL, 0.428 mole). After 2 hours, an additional portion of benzylsulfonyl chloride (16.4 g, 85.8 mmole) was added. The solution gradually warmed to ambient temperature and was stirred for 16 hours. The solids were filtered and the filtrate was concentrated under vacuum to give an oil. The oil was purified by flash column chromatography (silica gel; eluting with a gradient of 10–50% diethyl ether in dichloromethane) to give 19.8 g (68% yield) of the title compound as a white foam. Thin-layer chromatography gave an Rf=0.55 (silica gel; 27:3:1 dichloromethane/methanol/acetic acid).

Example 9
Preparation of N-benzylsulfonyl-norVal(cyclo)-Gly

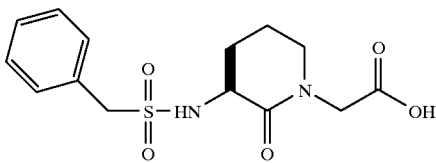

The compound of Example 8 (17.2 g, 52.7 mmole) was dissolved in 350 mL of methanol, cooled to 0° C., and treated with 1.0M lithium hydroxide in water (116 mL) dropwise. After 1 hour, the reaction mixture was allowed to warm to ambient temperature and was stirred for 18 hours. Dowex 50X8-400 ion-exchange resin ($H^{+\ form}$, 49 g) was added to the slurry to adjust the pH to 3. After stirring for 30 minutes, the slurry was filtered and the resin was washed with several portions of water/methanol. The filtrate was concentrated under vacuum. The resulting residue was taken up in acetonitrile and concentrated under vacuum. This was repeated one more time to give 17.2 g (100% yield) of the title compound as a colorless, amorphous solid. Thin-layer chromatography gave an Rf=0.30 (silica gel; 27:3:1 dichloromethane/methanol/acetic acid).

Example 10
Preparation of benzylsulfonyl-norVal(cyclo)-Gly-3-[3-piperidyl-(N-guanidino(bis-benzyloxycarbonyl))]-L-alaninol

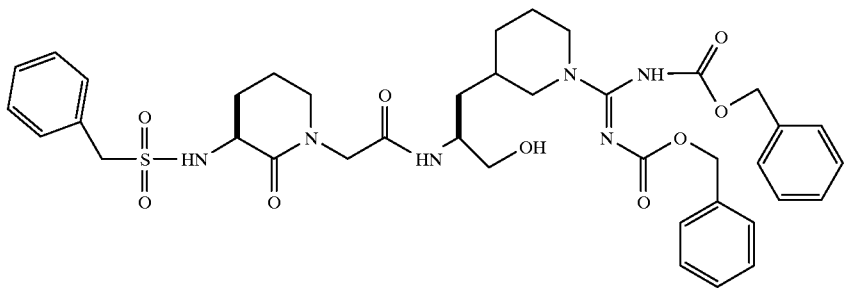

To a suspension of the compound of Example 5 (1.4 g, 2.8 mmole) in acetonitrile (10 mL) was added successively the compound of Example 9 (822 mg, 2.5 mmole), EDC (480 mg, 2.5 mmole), HOBt (402 mg, 2.62 mmole), dimethylaminopyridine (40 mg, 0.33 mmole) and triethylamine (12.5 mmole, 1.74 mL). The solution was stirred at ambient temperature for twelve hours. The solvent was removed under vacuum and the resulting residue was picked up in ethyl acetate (30 mL) and washed two times each with 10 mL portions of 1N sodium bisulfate, saturated sodium bicarbonate and brine. The organic layer was dried over anhydrous sodium sulfate and concentrated under vacuum to give crude product. This was chromatographed on a silica gel (230–400 mesh) column (5×40 cm) eluting with a 95:5 dichloromethane/methanol (two column volumes). 970 mg (78%) the title compound was obtained which consisted of a mixture of two diastereomers. Thin-layer chromatography gave an Rf=0.31 (silica gel; 95:5 dichloromethane/methanol).

Example 11
Preparation of Benzylsulfonyl-norVal(cyclo)-Gly-3-[3-piperidyl-(N-guanidino)]-L-alaninol, acetate salt

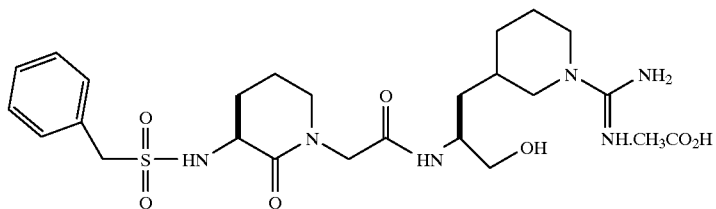

The compound of Example 10 (970 mg, 1.25 mmole) was subjected to catalytic hydrogenation in methanol (50 mL) and acetic acid (5 mL) in the presence of 10% palladium on carbon (90 mg) at 45 psi for 3 hours. The product was obtained as an oil in quantitative yield after removing the solvent under vacuum. Analytical HPLC using a 4.6×250 mm reverse phase column, containing a C-18 resin comprised of 10 micron size gel particles with a 300 angstrom pore size, using a gradient ranging from 10–25% acetonitrile in water (containing 0.1% trifluoroacetic acid) showed two peaks of equal intensity with retention times of 15 minutes at 16.5 minutes respectively. Fast atom bombardment mass spectrometry confirmed the theoretical molecular weight of 508.

Example 12
Preparation of benzylsulfonyl-norval(cyclo)-Gly-3-[3-piperidyl-(N-guanidino)]-L-alaninal

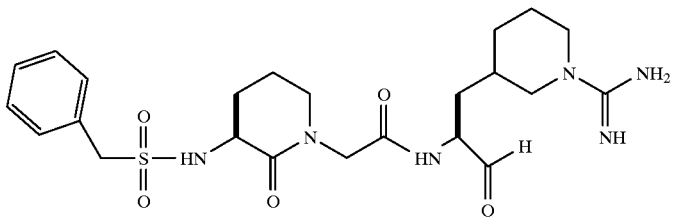

To a chilled solution of the compound of Example 11 (730 mg, 1.3 mmole) in dimethylsulfoxide and toluene (20 mL each) was added dichloroacetic acid (0.59 mL, 7.1 mmole) followed by EDC (2.75 g, 14.3 mmole) at one minute later. The reaction was stirred for 5 minutes at 0° C. and for 85 minutes at ambient temperature, and then was quenched with 50 mL water. The water layer was extracted twice with diethyl ether (15 mL portions), diluted to 100 mL of water and subjected to HPLC using a 47×300 mm reverse phase column, containing a C-18 resin comprised of 10 micron-size gel particles with a 300 angstrom pore size, eluting with a gradient ranging from 10–20% acetonitrile in water (containing 0.1% trifluoroacetic acid). The two diastereomers obtained had retention times of 16 (referred to as isomer "12A") and 18 minutes (referred to as isomer "12B") respectively. 180 mg of the faster-moving diastereomer, 229 mg of the slower-moving diastereomer and 95 mg of a mixture of the two diastereomers of the title compounds were recovered. Fast atom bombardment mass spectrometry confirmed the theoretical molecular weight of 506 for both diastereomers.

Example 13
Preparation of (S)-3-[(tert-butoxycarbonyl)amino]-1-azepine-2-one.

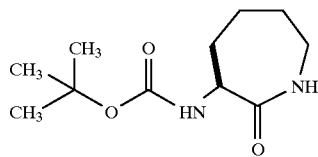

To a solution of L-(-)-alpha-amino-epsilon-caprolactam (24.36 g, 0.19 mole), obtained from Sigma, in 200 mL tetrahydrofuran and 200 mL of saturated sodium bicarbonate solution at 0C was added di-t-butyl dicarbonate (43.54 g, 0.20 mol) rapidly over 2 minutes. The mixture was stirred rapidly and was allowed to slowly warm to room temperature. After stirring was continued for 3 days, the volatiles were removed in vacuo, solid sodium chloride was added to saturate the aqueous phase, and it was extracted with 3×200 ml portions of ethyl acetate. The combined organic phase was washed with 2×50 mL water, 1×50 mL brine, dried over anhydrous magnesium sulfate, and evaporated to afford 37.92 g of crude product as a pale yellow solid. The combined aqueous layer was back-extracted with 200 mL of ethyl acetate, 200 mL of 20% isopropanol in dichloromethane, and dried to afford an additional 4.64 g of crude product, combined crude yield, 98%. The materials thus obtained were judged pure by TLC (Silica Gel; ethyl acetate, Rf=0.4) These were combined and recrystallized from ethyl acetate/hexanes to afford the product as a pale yellow crystalline solid, m.p. 148–150° C.

Example 14
Preparation of (S)-3-[(tert-butoxycarbonyl)amino]-2-oxo-1-azepineacetic acid, benzyl ester.

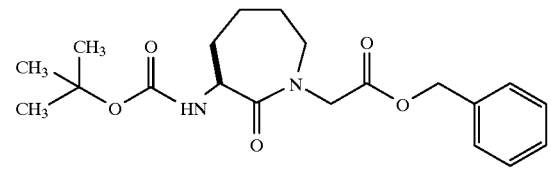

To a solution of the compound of Example 13 ( 12.28 g, 0.054 mol) in 215 mL dry tetrahydrofuran at ambient temperature under a $N_2$ atmosphere was added lithium bis(trimethylsilyl)amide (70.0 mL of 1M solution in tetrahydrofuran, Aldrich, 0.070 mole) dropwise rapidly so as to maintain ~30° C. The addition required about 20 minutes. The solution was stirred for 15 minutes and then a solution of benzyl bromoacetate (24.65 g, 0.108 mole, 17.1 mL) in 35 mL tetrahydrofuran was added rapidly so as to maintain ~32° C. After 18 hours reaction time, the mixture was quenched with 100 mL saturated ammonium chloride solution, diluted with 600 mL of ethyl acetate, and extracted with 2×50 mL water, 1×50 mL brine, dried over anhydrous magnesium sulfate and evaporated. The crude product was purified by flash chromatography on silica gel eluting with a gradient system of 4:1 to 2:1 hexane/ethyl acetate to afford 17.41 g (86% yield) of product as a viscous yellow oil; TLC (silica gel; 1:1 ethyl acetate/hexane): Rf=0.4.

Example 15
Preparation of (S)-3-amino-2-oxo-1-azepineacetic acid, benzyl ester hydrochloride.

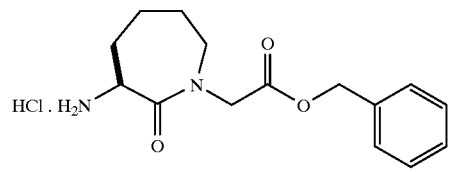

A solution of compound of Example 14 (17.04 g, 0.0453 mole) in 50 mL of ethyl acetate at 0° C. was treated with 5N HCl in ethyl acetate (117 mL, freshly prepared, 0.585 mole) in one portion. The solution was stirred at 0° for 10 minutes and then allowed to stir at ambient temperature for 1.5 hours. The solvent was removed in vacuo, dry acetonitrile (200 mL) was added and the solvents were reevaporated. The residue was pumped at <1 mm Hg on a vacuum pump for several hours to afford 14.06 g (99.3% yield) of product as a pale yellow foam, judged pure by TLC (silica gel; 27:3:1 dichloromethane/methanol/concentrated ammonium hydroxide): Rf=0.4.

Example 16
Preparation of (S)-3-benzylsulfonylamido-2-oxo-1-azepineacetic acid, benzyl ester.

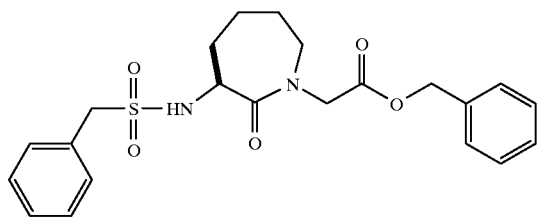

To a solution of compound of Example 15 (9.38 g, 0.030 mole) in 300 mL dry acetonitrile was added benzylsulfonyl chloride (6.29 g, 0.033 mole) and the solution was cooled to 0° C. under N$_2$. A solution of triethylamine (6.68 g, 0.066 mole, 9.20 mL) dissolved in 25 mL dry acetonitrile was added dropwise so as to maintain <5° C. The resultant mixture was stirred at 0° C. for 1 hour and then allowed to stir at ambient temperature for 9 hours. Additional portions of benzylsulfonyl chloride (572.0 mg, 3.0 mmole) and triethylamine (0.92 g, 9.0 mmole, 1.27 mL) were added, the mixture was stirred for 14 hours, filtered, and evaporated. The residue was purified by flash chromatography on silica gel using a gradient system of dichloromethane to 10% ethyl acetate in dichloromethane to afford 11.10 g (86% yield) of product as a stiff yellow oil, judged pure by TLC (silica gel; 9:1 dichloromethane/ethyl acetate): Rf=0.4.

Example 17
Preparation Qf (S)-3-benzylsulfonylamido-2-oxo-1-azepineacetic acid ("BnSO$_2$-norLeu(cyclo)-Gly").

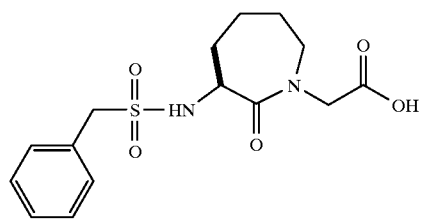

To a solution of Example 16 (11.06 g, 0.0257 mole) in 200 mL ethanol was added 10% Pd/C (1.11 g) and the mixture was hydrogenated at 40 psi on the Parr Shaker for 5 hours. The catalyst was filtered off and the solvents were removed to afford 8.81 g (~quantitative yield) of product as a colorless foam, judged pure by TLC (silica gel: 27:3:1 dichloromethanel methanol/acetic acid): Rf=0.5.

Example 18

Preparation of N-(BnSO$_2$-norLeu(cyclo)-Gly)-3-[3-piperidyl-(N-guanidino(bis-benzyloxycarbonyl))]-alaninol.

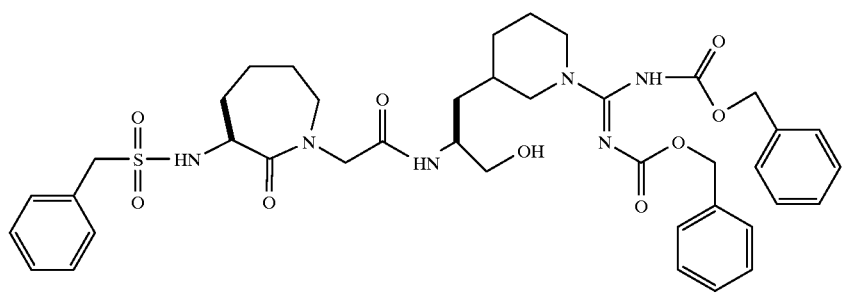

To a suspension of the compound of Example 5 (266 mg, 0.45 mmole) in acetonitrile (7 mL) was added successively the compound of Example 17 ((S)-3-benzylsulfonylamido-2-oxo-1-azepineacetic acid) (133 mg, 0.41 mmole), 1-ethyl-3-(3-dimethylamino-propyl)carbodiimide hydrochloride salt (86 mg, 0.45 mmole), 1-hydroxybenzotriazole hydrate (72 mg, 0.47 mmole) and diisopropylethylamine (2.44 mmole, 417 microliters). The solution was stirred at ambient temperature for twelve hours. The solvent was removed under reduced pressure and the remaining residue was picked up in ethyl acetate (15 mL) and washed two times each with 10 mL portions of 1N sodium bisulfate, saturated sodium bicarbonate and saturated sodium chloride solution. The organic layer was dried over sodium sulfate and concentrated to crude product. The crude product was subjected to flash column chromatography on 6 inches of silica gel (230–400 mesh) using a 2.5×56 cm column. The column was eluted with ethyl acetate (two column volumes), followed by ethyl acetate containing 1% acetic acid. The pure product, obtained as an oil, had an R$_f$ value of 0.33 in ethylacetate.

Example 19
Preparation of N-(BnSO$_2$-norLeu(cyclo)-Gly)-3-[3-piperidyl-(N-guanidino)]alaninol, acetate salt.

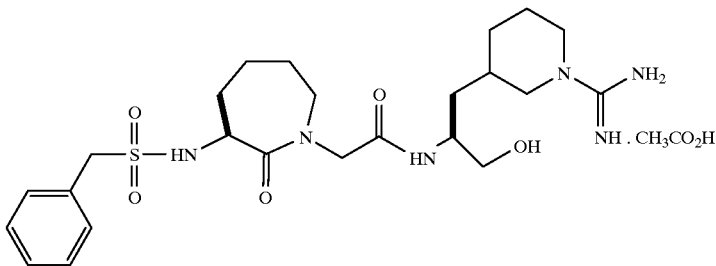

The compound of Example 18 (130 mg, 0.16 mmole) was subjected to catalytic hydrogenation in methanol (8 mL), and acetic acid (2 mL) and water (2 mL) in the presence of palladium on carbon (20 mg) at 40 psi for 4 hours. The product was obtained as an oil in quantitative yield. Analytical HPLC in a 10% to 20% acetonitrile in water (0.1% trifluoroacetic acid) showed two peaks with retention times of 17.5 minutes and 19 minutes, respectively. MH+ obtained for the product is 523.

Example 20

Preparation of N-(BnSO$_2$-norLeu(cyclo)-Gly)-3-[3-piperidyl-(N-guanidino)]alaninal.

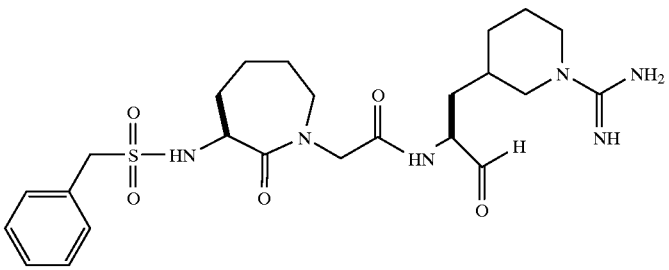

To a chilled solution of the compound of Example 19 (110 mg, 0.19 mmole) in dimethylsulfoxide and toluene (2 mL each) was added dichloroacetic acid (78 microliter, 0.94 mmole) followed by 1-ethyl-3-(3-dimethylamino-propyl) carbodiimide hydrochloride salt (0.36 g, 1.9 mmole) at one minute later. The reaction was stirred for 5 minutes at 0° C. and 85 minutes at ambient temperature, and quenched with 30 mL water. The water layer was extracted twice with diethyl ether (15 mL portions), diluted to 60 mL with water and subjected to high pressure liquid chromatography using a reverse phase column containing a C-18 resin comprised of 10 micron-size gel particles with a 300 angstrom pore size. The column was eluted with a water/acetonitrile (containing 0.1% trifluoroacetic acid) gradient where the gradient was run from 10% to 30% acetonitrile. In analytical HPLC using a C18 reverse phase column, the two diastereomers of the product obtained had retention times of 13 minutes and 13.5 minutes, respectively, in a 5% to 50% acetonitrile gradient. 11.1 mg of the faster moving isomer and 23 mg of the slower moving isomer were recovered from the preparative HPLC purification. MH+ obtained was 521 for both isomers.

Example 21

Preparation of semicarbazid-4-yl diphenylmethane, trifluoroacetate salt.

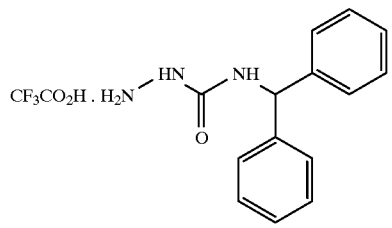

Step 1:

A solution of carbonyldiimidazole (16.2 g, 0.10 mole) in 225 mL of dimethylformamide was prepared at room temperature and allowed to stir under nitrogen. A solution of t-butyl carbazate (13.2 g, 0.100 moles) in 225 mL dimethylformamide was then added dropwise over a 30 minute period. Next, diphenylmethylamine (18.3 g, 0.10 moles) was added over a 30 minute period. The reaction was allowed to stir at room temperature under nitrogen for one hour. Water (10 mL) was added and this mixture was concentrated to about 150 mL under vacuum. This solution was poured into 500 mL water and extracted with 400 mL of ethyl acetate. The ethyl acetate phase was extracted two times each with 75 mL 1N HCl, water, saturated sodium bicarbonate and brine, and then was dried with anhydrous magnesium sulfate. The mixture was filtered and the solution was concentrated to give 29.5 g (85% yield) of 1-t-butoxycarbonyl-semicarbazid-4-yl diphenylmethane as a white foam. This material may be purified by recrystallization from ethyl acetate/hexane, but was pure enough to use directly in step 2: mp 142–143° C. $^1$H NMR (CDCl$_3$) delta 1.45 (s, 9H), 6.10 (dd, 2H), 6.42 (s, 1H), 6.67 (bs, 1H), 7.21–7.31 (m, 10H). Anal. Calc'd. for C$_{19}$H$_{23}$N$_3$O$_3$: C, 66.84; H, 6.79; N, 12.31. Found: C, 66.46; H, 6.75; N; 12.90.

Step 2:

A solution of 3.43 g (10 mmole) of 1-t-butoxycarbonyl-semicarbazid-4-yl diphenylmethane in 12.5 mL of dichloromethane was treated with 12.5 mL of trifluoroacetic acid at 0° C. The reaction mixture was allowed to stir for 30 minutes at this temperature. The reaction mixture was then added dropwise to 75 mL of diethyl ether to give a precipitate. The resulting precipitate was filtered off and washed with diethyl ether to give 2.7 g (80% yield) of the title compound; mp 182–184° C.

Example 22

Preparation of 3-thioamidobenzyl-N-acetylaminomalonic acid diethyl ester.

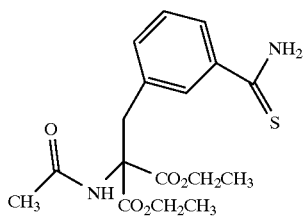

To a stirred solution of alpha-bromo-meta-tolunitrile (45.0 g, 0.24 mole), diethyl acetamidomalonate (48.0 g, 0.22 mole) and potassium iodide ((3.0 g, 0.018 mole) in dioxane (500 mL) was added 2.5M sodium ethoxide in ethanol (100 mL) dropwise under an argon atmosphere. After the addition was complete, the solution was refluxed for 6 hours. The reaction mixture was allowed to stand overnight at room temperature, then diluted with brine (250 mL) and water (250 mL), and extracted with ethyl acetate four times (1.0 L total). The combined extracts were washed with water (100 mL), 10% citric acid (100 mL), water (100 mL) and brine (2×50 mL), then dried over anhydrous magnesium sulfate and filtered; the solvent was removed under vacuum. The crude residue was recrystallized from ethyl acetate and diethyl ether in two crops to yield 43.51 g (60%) of the 3-cyanobenzyl-N-acetylaminomalonic acid diethyl ester as yellow crystals.

H$_2$S(g) was bubbled into a rapidly stirring solution of 3-cyanobenzyl-N-acetylaminomalonic acid diethyl ester (44.3 g, 0.13 mmole) in pyridine (300 mL) and triethylamine (100 mL) for 40 minutes. The reaction mixture was stirred at room temperature for 16 hours, then poured into 3.0 L of water. A yellow precipitate formed immediately. The solution was allowed to stand at 40° C. for 4 hours, then was filtered. The crude title compound was recrystallized from ethyl acetate and hexanes to yield 48.1 g (98%) of the title compound as yellow crystals. m.p. 183–186° C. $^1$H NMR (CDCl$_3$): delta 1.31 ( t, J=7.1 Hz, 6H), 2.06 (s, 3H), 3.70 (s, 2H), 4.29 (g, J=7.1 Hz, 4H), 4.80–4.87 (m, 1H), 6.60 (s, 1H), 7.10–7.20 (m, 1H), 7.27–7.35 (m, 2H), 7.60–7.70 (m, 2H). Anal. Calc'd for C$_{17}$H$_{22}$N$_2$O$_5$S: C, 55.72; H, 6.05; N, 7.64. Found: C, 55.55; H, 5.96; N, 7.76.

Example 23

Preparation of 3-amidino-D,L-phenylalanine, dihydrochloride salt.

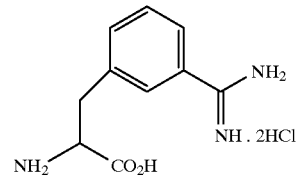

The compound of Example 22 (48.1 g, 0.13 mmole) was dissolved in acetone (800 mL). Iodomethane (18.3 mL, 0.19 mole, 1.5 equivalents) was added, and the solution was refluxed for 30 minutes. The solution was cooled to room temperature, and the intermediate thioimidate was filtered, dried and dissolved in methanol (500 mL). Ammonium acetate (14.8 g, 0.19 mole, 2 equivalents) was added. The reaction mixture was refluxed for 1 hour, then cooled to room temperature, and poured into ether (1.2 L). The solution was allowed to stand at 4° C. for 72 hours. The crude 3-amidinobenzyl-N-acetylaminomalonic acid diethyl ester was filtered, washed with ether, air dried, and then refluxed in concentrated HCl (250 mL) for 3 hours. The reaction mixture was concentrated under vacuum, diluted with water (0.5 L), and concentrated under vacuum again. These steps were repeated. The crude title compound was purified by cation-exchange (Sephadex SP-C25) using a gradient of 0–1.0N HCl as eluent to yield 10.8 g (30%) of the title compound as an off-white solid. $^1$H NMR (D$_2$O): delta 3.14–3.29 (2H, m), 4.17 (dd, J=7.4, 6.2 Hz, 1H), 7.42–7.69 (4H, m). Anal. Calc'd for C$_{10}$H$_{13}$N$_3$O$_2$.2HCl.1.9H2O: C, 38.20; H, 6.03; N, 13.36. Found: C, 38.51; H, 5.64; N, 12.89.

Example 24

Preparation of N-alpha-Boc-N-omega-4-methoxy-2,3,6-trimethylbenzenesulfonyl-3-amidino-D L-phenylalanine.

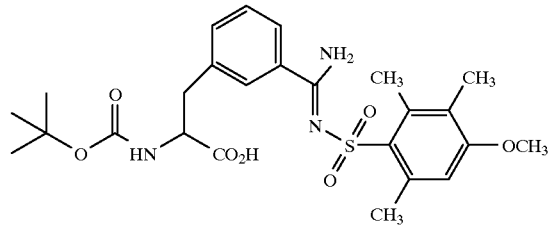

The compound of Example 23 (3-amidino-D,L-phenylalanine) (4.00 g, 13 mmole) was dissolved in 50% aqueous dioxane (20 mL). Sodium bicarbonate (3.38 g, 40 mmole) was added, followed by di-t-butyl dicarbonate (2.93 g, 13 mmole) in dioxane (4 mL). The reaction mixture was stirred for 18 hours at room temperature. The solution was cooled in an ice bath, and 4.0N sodium hydroxide was added dropwise until the solution was pH 12. 4-methoxy-2,3,6-trimethylbenzenesulfonyl chloride (8.01 g, 32 mmole) in dioxane (10 mL) was added dropwise. 4.0N sodium hydroxide was added as needed to keep the pH at 12. The ice bath was removed. After 1 hour, 1.0N HCl was added to bring the solution to pH 7–8. The solution was diluted with an additional 50 mL of water and then was washed with ethyl acetate two times (20 mL each). The aqueous layer was acidified to pH 1.0 with 1.0N HCl and extracted with ethyl acetate three times (100 mL total). The combined organic layers were washed with water (20 mL) and brine twice (10 mL each). The organic layer was dried over anhydrous magnesium sulfate and the solvent was removed under vacuum. The residue was dissolved in a minimum amount of dichloromethane, then added dropwise to ether (25 mL). Solid impurities were removed by filtering and the solvent removed from the filtrate under vacuum to give 4.90 g (68% crude yield) of the title compound as an off-white foam. A 30 mg sample of the title compound was further purified by preparative thin-layer chromatograph developing with 1% acetic acid/5% isopropanol/dichloromethane to give 9 mg of the title compound in a purer form. Rf=0.16 (1% acetic acid/5% isopropanol/dichloromethane). $^1$H NMR (CD$_3$OD): delta 1.32 (s, 9H), 2.14 (s, 3H), 2.63 (s, 3H), 2.71 (s, 3H), 2.93 (dd, J=13.7, 9.3 Hz, 1H), 3.22 (dd, J=13.7, 4.3 Hz, 1H), 3.85 (s, 3H), 4.34–4.37 (m, 1H), 6.72 (s, 1H), 7.35–7.47 (2H, m), 7.69–7.75 (m, 2H).

Example 25

Preparation of N-alpha-Boc-N-omega-4-methoxy-2,3,6-trimethylbenzenesulfonyl-3-amidino-D,L-phenylalanine-N-methyl-O-methyl-carboxamide.

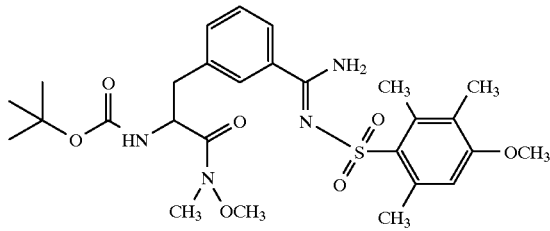

To a stirred solution of compound of Example 24 (1.00 g, 1.92 mmole), O,N-dimethyl hydroxylamine hydrochloride (375 mg, 3.85 mmole), hydroxybenzotriazole hydrate (294 mg, 1.92 mmole) and 4-methylmorpholine (1.06 mL, 9.62 mmole) in tetrahydrofuran (4 mL), cooled in an ice bath, was added EDC (406 mg, 2.12 mmole). The ice bath was removed, and the reaction mixture was stirred for 2 hours at room temperature. The reaction mixture was diluted with ethyl acetate (75 mnL), washed with water, 10% citric acid, water, saturated sodium bicarbonate, and brine. The organic layer was dried over anhydrous magnesium sulfate and the solvent was removed under vacuum. 750 mg (69%) of the title compound was isolated. $^1$H NMR (CDCl$_3$): delta 1.33 (s, 9H), 2.14 (s, 3H), 2.66 (s, 3H), 2.75 (s, 3H), 2.80–2.88 (m, 1H), 3.06–3.20 (m, 4H), 3.70 (s, 3H), 3.84 (s, 3H), 4.98–5.06 (m, 1H), 5.21 (d, J=8.7 Hz, 1H), 6.48 (bs, 1H), 6.58 (s, 1H), 7.30–7.34 (m, 2H) 7.60–7.68 (m, 2H), 8.11 (bs, 1H). Anal. Calc'd for C$_{27}$H$_{38}$N$_4$O$_7$S. 0.5H2O: C, 56.73; H, 6.88; N, 9.80. Found: C, 56.97; H, 6.66; N, 9.43.

Example 26

Preparation of N-alpha-Boc-N-omega-4-methoxy-2,3,6-trimethylbenzenesulfonyl-D,L-3-amidinophenylalaninal.

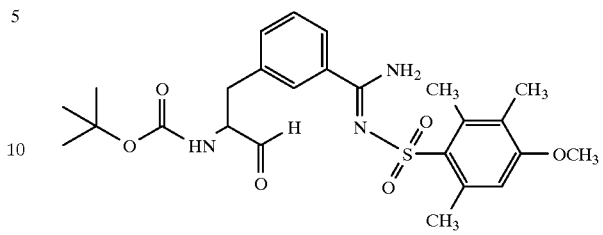

To a stirred solution of LiAlH$_4$ (2.00 mL of a 1.0M solution in tetrahydrofuran, 1.24 mmole) in tetrahydrofuran (8 mL), cooled in a dry ice/acetone bath, the compound of Example 25 (0.75 g, 1.9 mmole in tetrahydrofuran (5 mL)) was added dropwise. The cooling bath was removed and the reaction mixture was allowed to warm to 5° C. The reaction mixture was re-cooled in the dry ice acetone bath and quenched with 3.0 mL of a 1:2.7 wt./wt. solution of potassium bisulfate in water. The reaction mixture was allowed to warm to room temperature, stirred for 3 hours, filtered and concentrated under vacuum. The residue was dissolved in ethyl acetate (20 30 mL), and washed with 10% citric acid (2 mL), water (2 mL), saturated sodium bicarbonate (2 mL) and brine (2 mL). The organic layer was dried over anhydrous magnesium sulfate and the solvent was removed under vacuum to yield 580 mg (86%) of the title compound. $^1$H NMR (CDCl$_3$): delta 1.31 (s, 9H), 2.07 (s, 3H), 2.57 (s, 3H), 2.67 (s, 3H),2.90–3.17 (2H, m), 3.77 (s, 3H), 4.33–4.40 (1H, M), 5.02–5.08 (1H, m), 6.48 (1H, S), 7.23–7.31 (2H, m), 7.50–7.62 (2H, m), 7.94, (1H, bs), 8.05 (1H, bs), 9.55 (1H, s). Anal. Calc'd for C$_{25}$H$_{33}$N$_3$O$_6$S.0.5H2O: C, 58.58; H, 6.69; N,8.20. Found: C, 58.57; H. 6.72; N, 7.98.

Example 27

Preparation of N-alpha-Boc-N-omega-4-methoxy-2,3,6-trimethylbenzenesulfonyl-D,L-3-amidinoxhenylalaninal-semicarbazonyl-4-N-diphenylmethane.

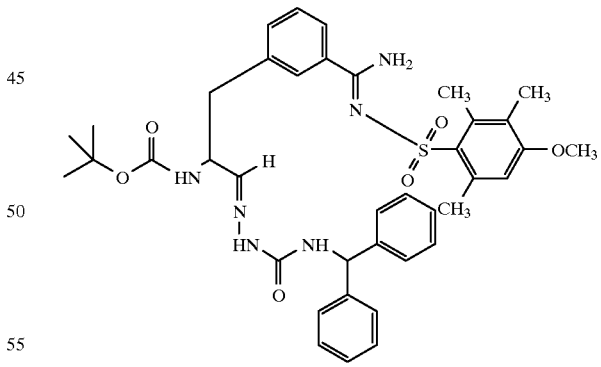

The compound of Example 26 (0.58 g, 1.9 mmole), the compound of example 20 (410 mg, 1.15 mmole) and sodium acetate trihydrate (188 mg, 1.38 mmole) were refluxed in 75% aqueous ethanol (10 mL) for 1 hour. After the reaction mixture was cooled to room temperature, it was diluted with ethyl acetate (50 mL), washed with 1.0N HCl (5 mL), water (5 mL), saturated sodium bicarbonate (5 mL) and brine (2×5 mL), and dried over anhydrous magnesium sulfate. The solvent was removed under vacuum to yield 750 mg (89% yield) of the title compound as an off-white foam. Analysis calculated for $C_{39}H_{46}N_6O_6S \cdot 1.0H_2O$: C, 62.88; H, 6.49; N, 11.28. Found: C, 63.14; H, 6.35N, 11.10.

Example 28
Preparation of N-omega-4-methoxy-2,3,6-trimethylbenzene sulfonyl-D,L-3-amidinophenylalaninal-semicarbazonyl-4-N-diphenylmethane, trifluoroacetate salt.

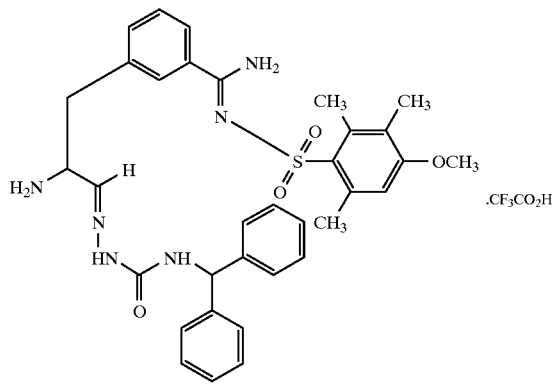

The compound of Example 27 (750 mg. 1.9 mmole) was treated with 50% trifluoroacetic acid/dichloromethane (3 mL) for 30 minutes at room temperature. The reaction mixture was added dropwise to ether (50 mL). The solution was allowed to stand at 4° C. for 18 hours. The product was filtered, and dried under vacuum to yield 600 mg (79% yield) of the title compound as an off-white solid. Analysis calculated for $C_{39}H_{46}N_6O_6S \cdot 1.3CF_3CO_2H$: C, 56.72; H. 5.11; N, 10.84. Found: C, 56.34; H, 5.47; N, 11.49.

Example 29
Preparation of BnSO$_2$-norLeu(cyclo)-Gly-D,L-N-omega-4-methoxy-2,3,6-trimethylbenzenesulfonyl-D,L-3-amidinophenyl alaninal-semicarbazonyl-4-N-diphenylmethane.

mmole) is added. After an additional 2 hours, the reaction mixture is diluted with water (25 mL) and brine (25 mL). The product is filtered and dissolved into ethyl acetate (25 mL). The solution is washed with 10% citric acid, water, saturated sodium bicarbonate and brine, and is dried over anhydrous magnesium sulfate. The solvent is removed under vacuum. The resulting residue is chromatographed by flash chromatography on silica gel to give the title compound.

Example 30
Preparation of BnSO$_2$-norLeu(cyclo)-Gly-D,L-3-amidinoohenyl alaninal semicarbazone.

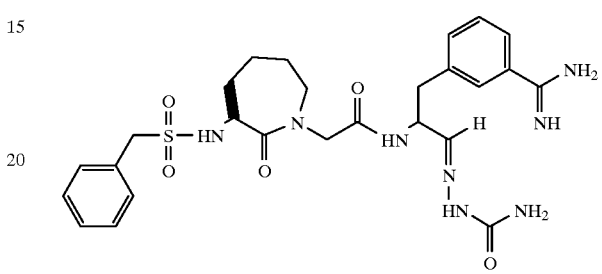

The compound of Example 29 (104 mg, 0.11 mmole) is treated with hydrofluoric acid/anisole (9:1) for 30 minutes at −20° C. and 0° C. for 30 minutes. After removal of the hydrofluoric acid, the resulting residue is dissolved in 20% aqueous acetic acid and washed with diethyl ether. The aqueous layer is lyophilized to a powder, then is purified by preparative HPLC (C-18, eluting with 10–40% acetonitrile-water gradient containing 0.1% trifluoroacetic acid) to give the title compound.

Example 31
Preparation of BnSO$_2$-norLeu(cyclo)-Gly-D,L-3-amidinophenyl alaninal.

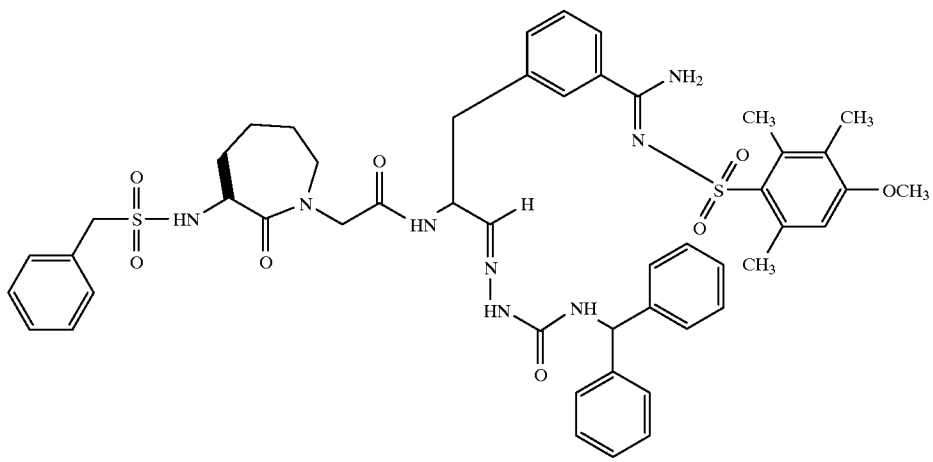

1-Ethyl-3-(3-dimethylamino-propyl)carbodiimide hydrochloride salt (94 mg, 0.94 mmole) is added in one portion to a stirred solution of the compound of Example 17 (180 mg, 0.49 mmole), hydroxybenzotriazole (75 mg, 0.49 mmole), and 4-methylmorpholine (0.24 mL, 2.2 mmole) in dimethylformamide (5 mL) with cooling in an ice bath. After 30 minutes, the compound of Example 28 (363 mg, 0.49

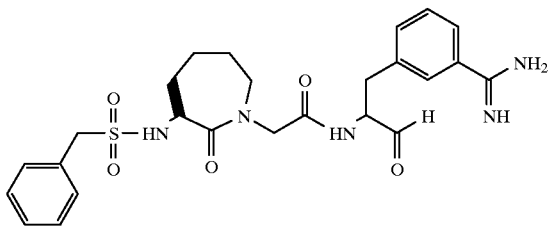

The compound of Example 30(17 mg, 30 micromole) is dissolved in methanol (1 mL) and 1% aqueous trifluoroacetic acid (5 mL), then formalin (0.23 mL) is added. After 40 minutes, the solution is filtered through a 2 micron filter, diluted to a volume of 15 mL with water, and then is purified by preparative HPLC (C-18, eluting with 10–40% acetonitrile-water gradient containing 0.1% trifluoroacetic acid). The fractions containing the title compound are pooled and lyophilized to give the title compound.

Example 32
Preparation of N-Boc-L-methionyl-glycine methyl ester

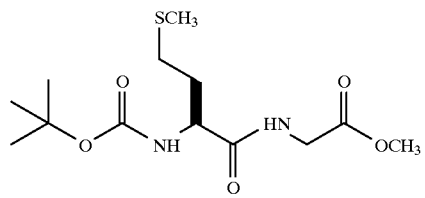

N-Alpha-Boc-methionine (24.9 g, 0.1 mole) and glycine methyl ester hydrochloride (12.6 g, 0.1 mole) were mixed in degassed dimethylformamide (150 mL). Triethylamine (13.9 mL, 0.1 mole) and HOBt (15.3 g, 0.1 mole) were dissolved in the mixture, and DCC (20.6 g, 0.1 mole) was added. The mixture was stirred at room temperature overnight and filtered. The filtrate was concentrated under vacuum, and the residue was redissolved in dichloromethane (150 mL). This solution was washed with 0.5M citric acid (3×50 mL) and 2N aqueous sodium bicarbonate (3×50 mL) and dried over anhydrous sodium sulfate. The solution was filtered, concentrated under vacuum, and recrystallized ethyl acetate/hexanes to give 24.1 g (75% yield) of the title product.

Example 33
Preparation of N-Boc-L-methionyl-alycine methyl ester methylsulfonium iodide

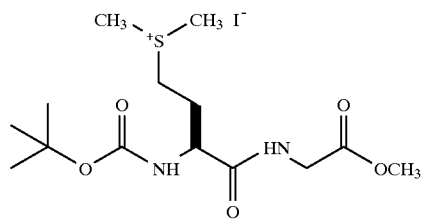

The compound of Example 32 (960 mg, 3 mmole) was dissolved with stirring in 6 mL of methyl iodide at room temperature. The reaction mixture was stirred for 6.5 hours over which time a gummy solid had separated. The supernatant was drawn off and the residue was dried under vacuum to give 1.41 g (100%) of the title compound as a hygroscopic foam.

Example 34
Preparation of (S)-3-Boc-amino-2-oxo-1-pyrrolidineacetic acid

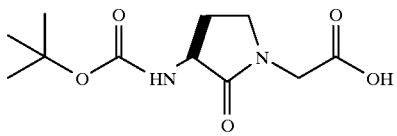

The compound of Example 33 (7.3 g, 15.6 mmole) was dissolved in 312 mL of 1:1 dimethylformamide/dichloromethane under nitrogen and cooled to 0° C. Sodium hydride (1.5 g of a 50% mineral oil suspension, 31.5 mmole) was added all at once, and the mixture was stirred at 0° C. for 2.5 hours. Ethyl acetate (104 mL) followed by water (24 mL) was added, and the resultant solution was left overnight at room temperature. The solution was concentrated under vacuum to a small volume and partitioned between water (50 mL) and dichloromethane (50 mL), The phases were separated, and the aqueous phase at pH 8 was acidified to pH 4 with 0.5M citric acid. Continuous extraction with dichloromethane, followed by concentration under vacuum, gave 2.06 g (51%) of the title compound as a crystalline solid.

Example 35
Preparation of N-(Benzyl-SO2-homoala(cyclo)-Gly)-3-[3-piperidyl-(N-guanidino)]-L-alaninal.

The compound of Example 34 is subjected to the analogous series of reactions described above for the conversion of the compound of example 6 to the target molecule of example 12 (esterification/protecting group cleavage; coupling with BnSO$_2$Cl, Et$_3$N; hydrolysis with LiOH; coupling with aminoalcohol of Example 5, EDC, HOBt, DMAP, Et$_3$N; hydrogenation with H$_2$, Pd/C, MeOH, HOAc, H$_2$O; and oxidation with DMSO, EDC, dichloroacetic acid, toluene) to afford the title lactam aldehyde of example 35

Example 36
General Procedure for Reaction of (S)-3-amino-2-oxo-hexahydro-1-azepineacetic acid, benzyl ester hydrochloride with Sulfonyl or Sulfamoyl Chlorides To a solution of the compound of Example 15 (9.38 g, 0.030 mole) in 300 mL dry acetonitrile is added the appropriate sulfonyl or sulfamoyl chloride listed below (0.033 mole) and the solution is cooled to 0° C. under N$_2$. A solution of triethylamine (6.68 g, 0.066 mole, 9.20 mL) dissolved in 25 mL dry acetonitrile is added dropwise so as to maintain <5° C. The resultant mixture is stirred at 0° C. for 1 hour and then is stirred at ambient temperature for about 2 to about 20 hours, filtered, and the solvent is evaporated in vacuo. The residue is purified by flash chromatography on silica gel using a gradient system of dichloromethane and 10% to about 50% ethyl acetate in dichloromethane to afford the product as a stiff yellow oil, judged pure by TLC (silica gel).

Using this method and the starting materials listed below, intermediates having the formula given below are made:

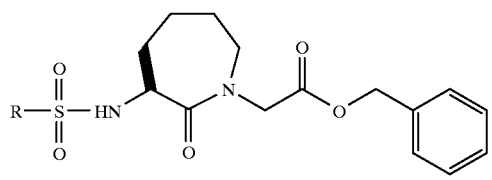

| R = | Starting material (amount needed) |
|---|---|
| phenyl | benzenesulfonyl chloride (5.83 g) |
| 1-naphthyl | 1-naphthylsulfonyl chloride (7.48 g) |
| 2-naphthyl | 2-naphthylsulfonyl chloride (7.48 g) |
| 2-carbomethoxyphenyl | 2-carbomethoxybenzenesulfonyl chloride (7.74 g) |
| 2-carbomethoxybenzyl | 2-carbomethoxybenzylsulfonyl chloride (8.21 g) |
| 2-trifluoromethylphenyl | 2-trifluoromethylbenzenesulfonyl chloride (8.07 g) |
| 2-trifluoromethylbenzyl | 2-trifluoromethylbenzylsulfonyl chloride (8.54 g) |
| 2-phenylethyl | 2-phenylethylsulfonyl chloride (6.75 g) |
| cyclohexylmethyl | cyclohexylmethylsulfonyl chloride (6.49 g) |
| cyclohexylamino | cyclohexylsulfamoyl chloride (6.52 g) |
| 2-thiophenemethyl | 2-Thiophenemethylsulfonyl chloride (6.49 g). This intermediate is prepared by reaction of 2-chloromethylthiophene (K.B. Wiberg, Org. Syntheses, 29, 31, 1949) with $Na_2SO_3$ to afford the corresponding sodium sulfonate salt (cf. S. Zuffanti, J. Am. Chem. Soc., 62, 1044, 1940), followed by standard treatment with $PCl_5$. |
| Perfluorobutyl | Perfluoro-1-butanesulfonyl fluoride (9.97 g) |
| Pentafluorobenzyl | Pentafluorobenzylsulfonyl chloride (9.26 g) |
| Phenylamino | Phenylsulfamoyl chloride (6.32 g) |
| 3-Carbomethoxy-benzyl | 3-Carbomethoxybenzyl-sulfonyl chloride (8.21 g) |
| 3-Trifluoromethyl-benzyl | 3-Trifluoromethylbenzyl-sulfonyl chloride (8.54 g) |
| 2-Methylbenzyl- | 2-Methylbenzylsulfonyl chloride (6.75 g) |
| 3-Methylbenzyl- | 3-Methylbenzylsulfonyl chloride (6.75 g) |
| 2-Methoxybenzyl- | 2-Methoxybenzylsulfonyl chloride (7.28 g) |
| 3-Methoxybenzyl- | 3-Methoxybenzylsulfonyl chloride (7.28 g) |
| 3-Chlorobenzyl- | 2-Chlorobenzylsulfonyl chloride (7.43 g) |
| 3-Chlorobenzyl- | 3-Chlorobenzylsulfonyl chloride (7.43 g) |
| 2-Methyl-5-fluoro-benzyl- | 2-Methyl-5-fluorobenzyl-sulfonyl chloride (7.35 g) |
| 2-Methyl-5-methoxy-benzyl- | 2-Methyl-5-methoxybenzyl-sulfonyl chloride (7.75 g) |
| 3-Carbomethoxy-5-methoxy-6-trifluoro-methyl benzyl- | 3-Carbomethoxy-5-methoxy-6-trifluoromethylbenzyl sulf-onyl chloride (11.44 g) |

Example 37
General Procedure for Preparation of Compounds of the Present Invention.

Following the five-step protocol outlined in Examples 16 through 20 (coupling with $RSO_2Cl$, $Et_3N$; hydrogenation with $H_2$, Pd/C; coupling with aminoalcohol of example 5, EDC, HOBt, DMAP, $Et_3N$; hydrogenation with $H_2$, Pd/C, MeOH, HOAc, $H_2O$; and oxidation with DMSO, EDC, dichloroacetic acid, toluene), the intermediates of Example 36 are used to synthesize the following compounds of the present invention (as their trifluoroacetate salts)

N-(phenyl-SO2-norLeu(cyclo)Gly)-3-[3-piperidyl-(N-guanidino)]-L-alaninal (Example 37a), N-(1-naphthyl-$SO_2$-norLeu(cyclo)-Gly)-3-[3-piperidyl-(N-guanidino)]-L-alaninal (Example 37b), N-(2-naphthyl-$SO_2$-norLeu(cyclo)-Gly)-3-[3-piperidyl-(N-guanidino)]-L-alaninal (Example 37c), N-(2-carbomethoxyphenyl-$SO_2$-norLeu(cyclo)-Gly)-3-[3-piperidyl-(N-guanidino)]-L-alaninal (Example 37d), N-(2-carbomethoxybenzyl-$SO_2$-norLeu(cyclo)-Gly)-3-[3-piperidyl-(N-guanidino)]-L-alaninal (Example 37e), N-(2-trifluoromethylphenyl-$SO_2$-norLeu(cyclo)-Gly)-3-[3-piperidyl-(N-guanidino)]-L-alaninal (Example 37f), N-(2-trifluoromethylbenzyl-$SO_2$-norLeu(cyclo)-Gly)-3-[3-piperidyl-(N-guanidino)]-L-alaninal (Example 37g), N-(phenylethyl-$SO_2$-norLeu(cyclo)-Gly)-3-[3-piperidyl-(N-guanidino)]-L-alaninal (Example 37h), N-(cyclohexylmethyl-$SO_2$-norLeu(cyclo)-Gly)-3-[3-piperidyl-(N-guanidino)]-L-alaninal (Example 37i), N-(cyclohexylamino-$SO_2$-norLeu(cyclo)-Gly)-3-[3-piperidyl-(N-guanidino)]-L-alaninal (Example 37j), N-(2-thiophenemethyl-$SO_2$-norLeu(cyclo)-Gly)-3-[3-piperidyl-(N-guanidino)]-L-alaninal (Example 37k), N-(perfluorobutyl-$SO_2$-norLeu(cyclo)-Gly)-3-[3-piperidyl-(N-guanidino)]-L-alaninal (Example 37l), N-(pentafluorobenzyl-$SO_2$-norLeu(cyclo)-Gly)-3-[3-piperidyl-(N-guanidino)]-L-alaninal (Example 37m), N-(phenylamino-$SO_2$-norLeu(cyclo)-Gly)-3-[3-piperidyl-(N-guanidino)]-L-alaninal (Example 37n), N-(3-carbomethoxybenzyl-$SO_2$-norLeu(cyclo)-Gly)-3-[3-piperidyl-(N-guanidino)]-L-alaninal (Example 37o), N-(3-trifluoromethylbenzyl-$SO_2$-norLeu(cyclo)-Gly)-3-[3-piperidyl-(N-guanidino)]-L-alaninal (Example 37p), N-(2-methylbenzyl-$SO_2$-norLeu(cyclo)-Gly)-3-[3-piperidyl-(N-guanidino)]-L-alaninal (Example 37q), N-(3-methylbenzyl-$SO_2$-norLeu(cyclo)-Gly)-3-[3-piperidyl-(N-guanidino)]-L-alaninal (Example 37r), N-(2-methoxybenzyl-$SO_2$-norLeu(cyclo)-Gly)-3-[3-piperidyl-(N-guanidino)]-L-alaninal (Example 37s), N-(3-methoxybenzyl-$SO_2$-norLeu(cyclo)-Gly)-3-[3-piperidyl-(N-guanidino)]-L-alaninal (Example 37t), N-(2-chlorobenzyl-$SO_2$-norLeu(cyclo)-Gly)-3-[3-piperidyl-(N-guanidino)]-L-alaninal (Example 37u), N-(3-chlorobenzyl-$SO_2$-norLeu(cyclo)-Gly)-3-[3-piperidyl-(N-guanidino)]-L-alaninal (Example 37v), N-(2-methyl-5-fluorobenzyl-$SO_2$-norLeu(cyclo)-Gly)-3-[3-piperidyl-(N-guanidino)]-L-alaninal (Example 37w), N-(2-methyl-5-methoxybenzyl-$SO_2$-norLeu(cyclo)-Gly)-3-[3-piperidyl-(N-guanidino)]-L-alaninal (Example 37x), N-(3-carbomethoxy-5-methoxy-6-trifluorbenzyl-$SO_2$-norLeu(cyclo)-Gly)-3-[3-piperidyl-(N-guanidino)]-L-alaninal (Example 37y), Example 38
Preparation of (S)-3-[(tert-Butoxycarbonyl)amino]-2-oxo-1-piperidineacetic acid, benzyl ester To a suspension of the compound of Example 6 (20.0 g, 0.0735 mol) in 700 mL of anhydrous acetonitrile and 30 mnL of anhydrous N,N-dimethylformamide was added anhydrous, powdered $K_2CO_3$ (12.68 g, 0.0918 mol) followed by benzyl bromide (13.81 g, 0.0808 mol, 9.61 mL). The mixture was stirred and vigorously refluxed for 6 hrs, cooled, filtered, and evaporated. The residue was purified by flash chromatography on silica gel eluting with a gradient system of 40 to 50% ethyl acetate/hexane to afford 25.50 g (96% yield) of product as a pale yellow oil; TLC (silica gel; ethyl acetate/hexane: 1,1 ): Rf=0.35.

Example 39
Preparation of (S)-3-Amino-2-oxo-1-piperidineacetic acid. benzyl ester hydrochloride To a solution of the compound of Example 38 (4.00 g, 0.0110 mole) in 10 mL of ethyl acetate at room temperature was added 5N HCl in ethyl acetate (50 mL, freshly prepared, 0.25 mole) in one portion. The solution was stirred for 3 hrs, solvent was evaporated, $CH_2Cl_2$ was added and the solvents were reevaporated. The residue was pumped at <1 mm Hg on a vacuum pump for 24 hours to afford 3.37 g (~Quantitative crude yield) of product as a colorless foam. TLC (silica gel; $CH_2Cl_2$, methanol, conc. $NH_4OH$: 27:3:1): Rf=0.32.

Example 40
General Procedure for Reaction of (S)-3-amino-2-oxopiperidine-1-acetic acid, benzyl ester hydrochloride with Sulfonyl or Sulfamoyl Chlorides To a solution of the compound of Example 39 (8.96 g, 0.030 mole) in 300 mL dry acetonitrile is added the appropriate sulfonyl or sulfamoyl chloride listed in Example 36 (0.033 mole) and the solution is cooled to 0° C. under $N_2$. A solution of triethylamine (6.68 g, 0.066 mole, 9.20 mL) dissolved in 25 mL dry acetonitrile is added dropwise so as to maintain <5° C. The resultant mixture is stirred at 0° C. for 1 hour and then is stirred at ambient temperature for about 2 to about 20 hours, filtered, and the solvent is evaporated in vacuo. The residue is purified by flash chromatography on silica gel using a gradient system of dichloromethane and 10% to about 50% ethyl acetate in dichloromethane to afford the product as a stiff yellow oil, judged pure by TLC (silica gel).

Using this method and the starting materials listed in Example 36, intermediates having the formula given below, with R defined as in Example 36, are made:

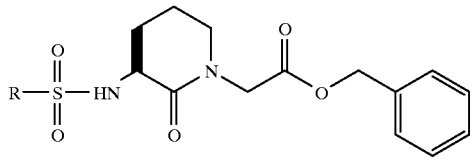

Example 41
General Procedure for Preparation of Compounds of the Present Invention.

Following the four-step protocol outlined in Examples 17 through 20 (hydrogenation with $H_2$, Pd/C; coupling with aminoalcohol of example 5, EDC, HOBt, DMAP, $Et_3N$; hydrogenation with $H_2$, Pd/C, MeOH, HOAc, $H_2O$; and oxidation with DMSO, EDC, dichloroacetic acid, toluene), the intermediates of example 40 are used to synthesize the following compounds of the present invention (as their trifluoroacetate salts):

N-(phenyl-SO$_2$-norVal(cyclo)Gly)-3-[3-piperidyl-(N-guanidino)]-L-alaninal (Example 41a),
N-(1-naphthyl-SO$_2$-norVal(cyclo)-Gly)-3-[3-piperidyl-(N-guanidino)]-L-alaninal (Example 41b),
N-(2-naphthyl-SO$_2$-norVal(cyclo)-Gly)-3-[3-piperidyl-(N-guanidino)]-L-alaninal (Example 41c),
N-(2-carbomethoxyphenyl-SO$_2$-norVal(cyclo)-Gly)-3-[3-piperidyl-(N-guanidino)]-L-alaninal (Example 41d),
N-(2-carbomethoxybenzyl-SO$_2$-norVa;1(cyclo)-Gly)-3-[3-piperidyl-(N-guanidino)]-L-alaninal (Example 41e),
N-(2-trifluoromethylphenyl-SO$_2$-norVal(cyclo)-Gly)-3-[3-piperidyl-(N-guanidino)]-L-alaninal (Example 41f),
N-(2-trifluoromethylbenzyl-SO$_2$-norVal(cyclo)-Gly)-3-[3-piperidyl-(N-guanidino)]-L-alaninal (Example 41g),
N-(phenylethyl-SO$_2$-norVal(cyclo)-Gly)-3-[3-piperidyl-(N-guanidino)]-L-alaninal (Example 41h),
N-(cyclohexylmethyl-SO$_2$-norVal(cyclo)-Gly)-3-[3-piperidyl-(N-guanidino)]-L-alaninal (Example 41i),
N-(cyclohexylamino-SO$_2$-norLValcyclo)-Gly)-3-[3-piperidyl-(N-guanidino)]-L-alaninal (Example 41j),
N-(2-thiophenemethyl-SO$_2$-norVal(cyclo)-Gly)-3-[3-piperidyl-(N-guanidino)]-L-alaninal (Example 41k),
N-(perfluorobutyl-SO$_2$-norVal(cyclo)-Gly)-3-[3-piperidyl-(N-guanidino)]-L-alaninal (Example 41l),
N-(pentafluorobenzyl-SO$_2$-norVal(cyclo)-Gly)-3-[3-piperidyl-(N-guanidino)]-L-alaninal (Example 41m),
N-(phenylamino-SO$_2$-norVal(cyclo)-Gly)-3-[3-piperidyl-(N-guanidino)]-L-alaninal (Example 41n),
N-(3-carbomethoxybenzyl-SO$_2$-norVal(cyclo)-Gly)-3-[3-piperidyl-(N-guanidino)]-L-alaninal (Example 41o),
N-(3-trifluoromethylbenzyl-SO$_2$-norVal(cyclo)-Gly)-3-[3-piperidyl-(N-guanidino)]-L-alaninal (Example 41p),
N-(2-methylbenzyl-SO$_2$-norVal(cyclo)-Gly)-3-[3-piperidyl-(N-guanidino)]-L-alaninal (Example 41q),
N-(3-methylbenzyl-SO$_2$-norVal(cyclo)-Gly)-3-[3-piperidyl-(N-guanidino)]-L-alaninal (Example 41r),
N-(2-methoxybenzyl-SO$_2$-norVal(cyclo)-Gly)-3-[3-piperidyl-(N-guanidino)]-L-alaninal (Example 41s),
N-(3-methoxybenzyl-SO$_2$-norVal(cyclo)-Gly)-3-[3-piperidyl-(N-guanidino)]-L-alaninal (Example 41t),
N-(2-chlorobenzyl-SO$_2$-norVal(cyclo)-Gly)-3-[3-piperidyl-(N-guanidino)]-L-alaninal (Example 41u),
N-(3-chlorobenzyl-SO$_2$-norLValcyclo)-Gly)-3-[3-piperidyl-(N-guanidino)]-L-alaninal (Example 41v),
N-(2-methyl-5-fluorobenzyl-SO$_2$-norVal(cyclo)-Gly)-3-[3-piperidyl-(N-guanidino)]-L-alaninal (Example 41w),
N-(2-methyl-5-methoxybenzyl-SO$_2$-norVal(cyclo)-Gly)-3-[3-piperidyl-(N-guanidino)]-L-alaninal (Example 41x),
N-(3-carbomethoxy-5-methoxy-6-trifluorbenzyl-SO$_2$-norLValcyclo)-Gly)-3-[3-piperidyl-(N-guanidino)]-L-alaninal (Example 41y).

Example 42
General procedure for reaction of (S)-3-amino 2-oxohexahydro-1-azepineacetic acid, benzyl ester hydrochloride with Phosphonochloridate derivatives The substituted phosphonochloridates listed below are prepared by methods described in the literature, see H. J. Musiol, F. Grams, S. Rudolph-Bohner and L. Moroder, J. Org. Chem., 51: 6144–6146 (1994) and references cited therein. To a solution of the compound of Example 15 (9.38 g, 0.030 mole) in 300 mL dry acetonitrile is added the appropriate phosphonochloridate derivative listed below (0.033 mole) and the solution is cooled to 0° C. under $N_2$. A solution of triethylamine (6.68 g, 0.066 mole, 9.20 mL) dissolved in 25 mL dry acetonitrile is added dropwise so as to maintain <5° C. The resultant mixture is stirred at 0° C. for 1 hour and then is stirred at ambient temperature for about 2 to about 20 hours, filtered, and the solvent is evaporated in vacuo. The residue is purified by flash chromatography on silica gel using a gradient system of dichloromethane and 10% to about 50% ethyl acetate in dichloromethane to afford the product as a stiff yellow oil, judged pure by TLC (silica gel).

Using this method and the starting materials listed below, intermediates having the formula given below are made

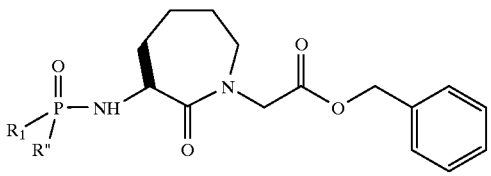

| $R_1$ = | R" = | Starting material (amount needed) |
|---|---|---|
| benzyl | OEt | BnPO(OEt)(Cl) (7.21 g) |
| benzyl | Me | BnPO(Me)(Cl) (6.22 g) |
| benzyl | NHMe | BnPO(NHMe)(Cl) (6.72 g) |
| benzyl | S-iPr | BnPO(S-i-Pr)(Cl) (8.21 g) |

Example 43
General Procedure for Preparation of Compounds of the Present Invention.

Following the four-step protocol outlined in examples 17 through 20 ( hydrogenation with $H_{b\ 2}$, Pd/C; coupling with aminoalcohol of example 5, EDC, HOBt, DMAP, $Et_3N$; hydrogenation with $H_2$, Pd/C, MeOH, HOAc, $H_2O$; and oxidation with DMSO, EDC, dichloroacetic acid, toluene), the intermediates of Example 42 are used to synthesize the following compounds of the present invention (as their trifluoroacetate salts).

N-(Benzyl-PO-(OEt)-norLeu(cyclo)-Gly)-3-[3-piperidyl-(N-guanidino)]-L-alaninal (Example 43a)

N-(Benzyl-PO-(Me)-norLeu(cyclo)-Gly)-3-[3-piperidyl-(N-guanidino)]-L-alaninal (Example 43b)

N-(Benzyl-PO-(NHMe)-norLeu(cyclo)-Gly)-3-[3-piperidyl-(N-guanidino)]-L-alaninal (Example 43c)

N-(Benzyl-PO-(S-iPr)-norLeu(cyclo)-Gly)-3-[3-piperidyl-(N-guanidino)]-L-alaninal (Example 43d)

Example A
Kinetic Analysis of $BzlSO_2$-norVal(cyclo)-Gly-Ala(3-guanPip)-al (Isomer B) in an in vitro Thrombin Inhibition Assay The ability of the compound of Example 12, $BzlSO_2$-norVal(cyclo)-Gly-Ala(3-guanPip)-al, isomer 12B, hereinafter referred to as "Isomer B", of the present invention to act as an inhibitor of thrombin catalytic activity was assessed by determining the inhibition constant, Ki.

Enzyme activity was determined using the chromogenic substrate Pefachrome t-PA ($CH_3SO_2$-D-hexahydrotyrosine-glycyl-L-Arginine-p-nitroanilide), obtained from Pentapharm Ltd. The substrate was reconstituted in deionized water prior to use. Purified human alpha-thrombin (3000U/mg specific activity) was obtained from Enzyme Research Laboratories, Inc. The buffer used for all assays was HBSA (10 mM HEPES, pH 7.5, 150 mM sodium chloride, 0.1% bovine serum albumin).

The assay for the Ki determination was conducted by combining in appropriate wells of a Corning microtiter plate, 50 microliters of HBSA, 50 microliters of Isomer B at a specified concentration diluted in HBSA (or HBSA alone for $V_o$ (uninhibited velocity) measurement), and 50 microliters of the chromogenic substrate (250 micromolar, 5-times Km) At time zero, 50 microliters of alpha-thrombin diluted in HBSA, was added to the wells yielding a final concentration of 0.5 nM in a total volume of 200 microliters. Velocities of chromogenic substrate hydrolysis which occurred over 40 min was measured by the change in absorbance at 405 nm using a Thermo Max® Kinetic Microplate Reader. The Ki value for Isomer B was determined using the relationships developed by Williams and Morrison, Methods in Enzymology, 63: 437 (1979) using steady state velocities (Vs) measured over 40 minutes. The extent of substrate hydrolysis was less than 5% over the course of this assay. Table 1 below gives the Ki values for Isomer B described in this patent. The data shows the utility of this compound as a potent in vitro inhibitor of human alpha-thrombin.

TABLE 1

Inhibitor Constant (Ki) of $BzlSO_2$-norVal(cyclo)-Gly-Ala(3-guanPip)-al (Isomer B) against human alpha-thrombin amidolytic activity.

| Compound | Ki (nM)* |
|---|---|
| Isomer B | 0.318 ± 16 |

* Mean ± SD, n = 3

Example B
In vitro Enzyme Assays for Specificity Determination

The ability of compounds of the present invention to act as a selective inhibitor of thrombin catalytic activity was assessed by determining the concentration of test compound which inhibited the activity of this enzyme by 50%, ($IC_{50}$), and comparing this value to that determined for some of the following related serine proteases: recombinant tissue plasminogen activator (rt-PA), plasmin, activated protein C, chymotrypsin, factor Xa, and trypsin.

The buffer used for all assays was HBSA (10 mM HEPES, pH 7.5, 150 mM sodium chloride, 0.1% bovine serum albumin). The assay for $IC_{50}$ determinations was conducted by combining in appropriate wells of a Corning microtiter plate, 50 microliters of HBSA, 50 microliters of test compound at a specified concentration (covering a broad concentration range) diluted in HBSA (or HBSA alone for $V_o$ (uninhibited velocity) measurement), and 50 microliters of the enzyme diluted in HBSA. Following a 30-minute incubation at ambient temperature, 50 microliters of the substrate at the concentrations specified below, was added to the wells yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a 50% decrease in the initial rate of hydrolysis was defined as the $IC_{50}$ value for that compound.

Thrombin Assay

Thrombin catalytic activity was determined using the chromogenic substrate Pefachrome t-PA ($CH_3SO_2$-D-hexahydrotyrosine-glycyl-L-arginine-p-nitroanilide, obtained from Pentapharm Ltd.). The substrate was made up in deionized water followed by dilution in HBSA prior to the assay in which the final concentration was 300 micromolar (about 5-times Km). Purified human alpha-thrombin was obtained from Enzyme Research Laboratories, Inc. The enzyme was diluted into HBSA prior to the assay in which the final concentration was 0.25 nM.

Recombinant tissue plasminogen activator (rt-PA)

rt-PA catalytic activity was determined using the substrate, Pefachrome t-PA ($CH_3SO_2$-D-hexahydrotyrosine-glycyl-L-arginine-p-nitroanilide, obtained from Pentapharm Ltd.). The substrate was made up in deionized water followed by dilution in HBSA prior to the assay in which the final concentration was 500 micromolar (about 3-times Km).

Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2251 [D-valyl-L-leucyl-L-lysine-p-nitroanilide], which was obtained from Kabi Diagnostica. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC)

aPC catalytic activity was determined using the chromogenic substrate, Pefachrome PC (delta-carbobenzloxy-D-lysine-L-prolyl-L-arginine-p-nitroanilide), obtained from Pentapharm Ltd.). The substrate was made up in deionized water followed by dilution in HBSA prior to the assay in which the final concentration was 250 micromolar (about 3-times Km). Purified human aPC was obtained from Hematologic Technologies, Inc. The enzyme was diluted into HBSA prior to assay in which the final concentration was 1.0 nM.

Chymotrpsin

Chymotrypsin catalytic activity was determined using the chromogenic substrate, S-2586 (methoxy-succinyl-L-arginine-L-prolyl-L-tyrosyl-p-nitroanilide), which was obtained from Kabi Diagnostica. The substrate was made up in deionized water followed by dilution in HBSA prior to the assay in which the final concentration was 100 micromolar (about 9-times Km). Purified (3x-crystallized;CDI) bovine pancreatic alpha-chymotrypsin was obtained from Worthington Biochemical Corp. The enzyme was reconstituted in deionized water and diluted into HBSA prior to assay in which the final concentration was 1.0 nM.

Trypsin

Trypsin catalytic activity was determined using the chromogenic substrate, S-2222 (benzoyl-L-isoleucine-L-glutamic acid- (gamma-methyl ester)-L-arginine-p-nitroanilide), which was obtained from Kabi Diagnostica. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Factor Xa

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, OH). All substrates were reconstituted in deionized water prior to use. The final concentration of S-2765 was 250 $\mu$M (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. Arch. Biochem. Biophys. 273:375–388 (1989)].

Table 2 lists the determined $IC_{50}$ values for Isomers A and B of Example 12 (columns A and B, respectively) and Isomers A and B of the Example 20 (columns C (faster eluting isomer) and D (slower eluting isomer), respectively) against certain of the enzymes listed above and demonstrates the high degree of specificity of this compound for the inhibition of a-thrombin compared to these related serine proteases.

Table 2. $IC_{50}$ value for the inhibition of thrombin amidolytic activity compared to selected serine proteases for compounds of the present invention $IC_{50}$ (nM)

| Enzyme | A | B | C | D |
|---|---|---|---|---|
| alpha-thrombin | 28.8 | 0.8 | 1.8 | 0.57 |
| rt-PA | NI | NI | >2500 | >2500 |
| Plasmin | >2500 | NI | >2500 | >2500 |
| aPC | NI | NI | >2500 | >2500 |
| Chymotrypsin | NI | NI | >2500 | >2500 |
| Trypsin | NI | NI | 11,200 | 34,400 |

NI-No inhibition observed at the maximal concentration of inhibitor assayed-25,000nM. The data represents the mean of at least two independent experiments.

Example C

Figure 4:
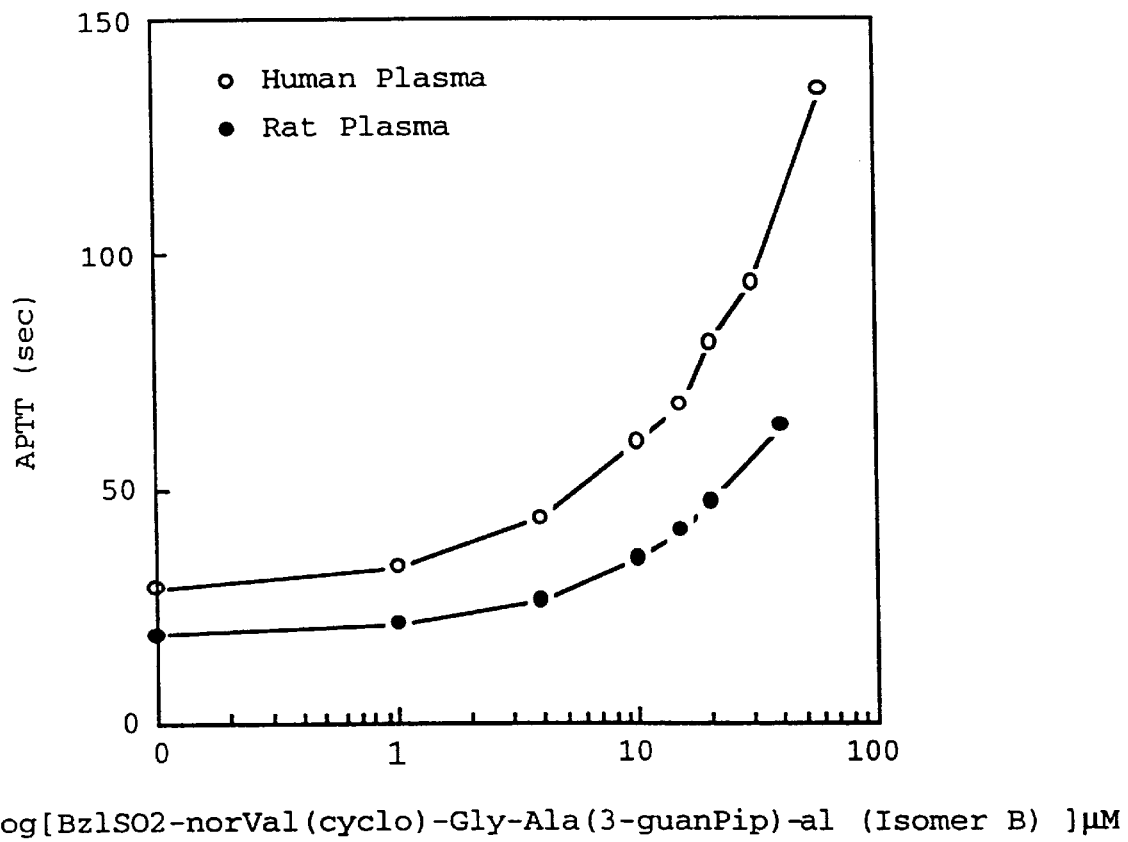
FIG. 4 depicts the anticoagulant effect of BzlSO$_2$-norVal (cyclo)-Gly-Ala(3-guanPip)-al (Isomer 26B) measured in citrated rat (●) and human (○) plasma using the activated partial thromboplastin time (APTT) assay. The control clotting times (0 inhibitor) for rat and human plasma were 19 seconds and 29 seconds, respectively. The concentration of BzlSO$_2$-norVal(cyclo)-Gly-Ala(3-guanPip)-al which caused a doubling of the control clotting time in rat and human plasma was 12.7 micromolar and 9.1 micromolar, respectively. The data is the mean of two independent determinations.

Ex vivo Anticoagulant Effects of $BzlSO_2$-norVal(cyclo)-Gly-Ala(3-guanPip)-al (Isomer B) in Rat and Human Plasma The ex vivo anticoagulant effects of Isomer B ($BzlSO_2$-norVal(cyclo)-Gly-Ala(3-guanPip)-al, Example 12) was determined by measuring the prolongation of the activated partial thromboplastin time (APTT) over a broad concentration range of the added inhibitor, using pooled normal human and rat plasma. Fresh frozen citrated pooled normal human plasma was obtained from George King Biomedical, Overland Park, KA. Pooled normal rat plasma was prepared from citrated whole blood collected from anesthetized rats using standard procedures. The plasma was flash frozen and stored at–80° C. until use. Measurements APTT was made using the Coag-A-Mate RA4 automated coagulometer (General Diagnostics, Organon Technica, Oklahoma City, Okla.) using the Automated APTT reagent (Organon Technica, Durham, N.C.) as the initiator of clotting according to the manufacturers instructions. The assay was conducted by making a series of dilution's of Isomer B in rapidly thawed plasma followed by adding 200 microliters to the wells of the assay carousel. As shown in FIG. 4, Isomer B prolonged the APTT in a dose dependent manner in both rat and human plasma demonstrating an anticoagulant effect in both species of mammals.

Example D

Evaluation of the Antithrombotic Potential of $BzlSO_2$-norVal(cyclo)-Gly-Ala(3-guanPip)-al (Isomer B) in an Experimental Rat Model of Thrombosis The demonstrated anticoagulant effects of Isomer B (Example 12; $BzlSO_2$-norVal(cyclo)-Gly-Ala(3-guanPip)-al) in both rat and human citrated plasma indicated that this compound may have potent antithrombotic effects in vivo. To investigate this, the antithrombotic (prevention of thrombus formation) properties of Isomer B was evaluated using the following established experimental model of acute vascular thrombosis.

Rat model of $FeCl_3$-induced platelet-dependent arterial thrombosis

This is a well characterized model of platelet dependent, arterial thrombosis which has been used in the evaluation potential antithrombotic compounds such as direct thrombin inhibitors. Kurz, K. D., Main, B. W., and Sandusky, G. E., Thromb. Res., 60: 269–280 (1990). In this model a platelet-rich, occlusive thrombus is formed in a segment of the rat carotid artery treated locally with a fresh solution of FeCl₃ absorbed to a piece of filter paper. The FeCl₃ is thought to diffuse into the treated segment of artery and causes de-endothelialization of the affected vessel surface. This results in the exposure of blood to subendothelial structures which in turn causes platelet adherence, thrombin formation and platelet aggregation resulting in occlusive thrombus formation. The effect of a test compound on the incidence of occlusive thrombus formation following the application of the FeCl₃ is monitored by ultrasonic flowtometry and is used as the primary end point. The use of flowtometry to measure carotid artery blood flow, is a modification of the original procedure in which thermal detection of clot formation was employed. Kurz, K. D., Main, B. W., and Sandusky, G. E., Thromb. Res., 60: 269–280 (1990).

Male Harlan Sprague Dawley rats (420–450 g) were acclimated at least 72 hours prior to use and fasted for 12 hours prior to surgery with free access to water. The animals were prepared, anesthetized with Nembutal followed by the insertion of catheters for blood pressure monitoring, drug and anesthesia delivery. The left carotid artery was isolated by making a midline cervical incision followed by blunt dissection and spreading techniques to separate a 2 cm segment of the vessel from the carotid sheath. A silk suture is inserted under the proximal and distal ends of the isolated vessel to provide clearance for the placement of a ultrasonic flow probe (Transonic) around the proximal end of the vessel. The probe is then secured with a stationary arm.

Following surgery the animals were randomized in either a control (saline) or treatment group with test compound (Isomer B) with at least 6 animals per group per dose. The test compound was administered as a single intravenous bolus at the doses outlined in Table 3 after placement of the flow probe and 5 minutes prior to the thrombogenic stimulus. At t=0, a 3 mm diameter piece of filter paper (Whatman #3) soaked with 10 microliters of a 35% solution of fresh FeCl₃ (made up in water) was applied the segment of isolated carotid artery distal to the flow probe. Blood pressure, blood flow, heart rate, and respiration were monitored for 60 minutes.

The incidence of occlusion (defined as the attainment of zero blood flow) was recorded as the primary end point and as a measure of the antithrombotic efficacy of Isomer B.

The antithrombotic efficacy of the Isomer B as an antithrombotic agent in preventing thrombus formation in this in vivo model was demonstrated by the reduction in the incidence of thrombotic occlusion as shown in Table 3 below.

TABLE 3

Evaluation of Isomer B in the FeCl₃ Model of Thrombosis in Rats.

| Treatment Group | Dose (mg/kg) | n | Incidence of Occlusion |
|---|---|---|---|
| Saline | — | 6 | 6/6 |
| Isomer B | 0.3 | 6 | 6/6 |
| Isomer B | 1.0 | 6 | 4/6 |
| Isomer B | 3.0 | 6 | 0/6* |

*-p ≤ 0.05 from saline control by Fishers test

The effective dose which prevents 50% of thrombotic occlusions in this model (ED₅₀) can be determined from the above data by plotting the incidence of occlusion versus the dose administered. This allows a direct comparison of the antithrombotic efficacy of Isomer B with other clinically effective antithrombotic agents which have also been evaluated in this model as described above. Table 4 lists the ED₅₀ values for several well known anticoagulant agents in this model compared to Isomer B.

TABLE 4

Efficacy of Isomer B compared to other antithrombotic agents based on ED₅₀ for thrombus prevention in the FeCl₃ model of arterial thrombosis.

| Compound | ED₅₀[a] (mg/k) | |
|---|---|---|
| Standard Heparin | 200 | U/kg |
| Argatroban | 3.8 | mg/kg |
| Hirulog ™ | 3.0 | mg/kg |
| Isomer B | 1.4 | mg/kg |

[a]ED₅₀ is defined as the dose that prevents the incidence of complete thrombotic occlusion in 50% of animals tested The data presented in Table 4 clearly demonstrates the effectiveness of Isomer B (BzlSO₂-norVal(cyclo)-Gly-Ala (3-guanPip)-al) in preventing occlusive thrombus formation in this experimental model. The relevance of this data to preventing human thrombosis can be inferred from the comparison to the other anticoagulant agents listed in this table which have been evaluated in an identical manner in this experimental model and have demonstrated antithrombotic efficacy in preventing thrombus formation clinically as described in the following literature citations: Heparin: Hirsh, J. N., Engl. J. Med., 324: 1565–1574 1992, Cairns, J. A. et. al., Chest, 102: 456–481S (1992); Argatroban: Gold, H. K. et.al., J. Am. Coll. Cardiol., 21: 1039–1047 (1993); and Hirulog™: Sharma, G. V. R. K. et.al., Am. J. Cardiol., 72: 1357–1360 (1993) and Lidón, R. M. et.al., Circulation, 88: 1495–1501 (1993). The in vivo comparison of Isomer B with the clinically effective antithrombotic agents Standard Heparin, Argatroban, and Hirulog™ in the same rodent model of experimental thrombosis coupled with the demonstrated anticoagulant effects of Isomer B in both rat and human plasma described above would lead one skilled in the art to conclude that this compound will be an effective antithrombotic agent in humans.

We claim:
1. A compound of the formula:

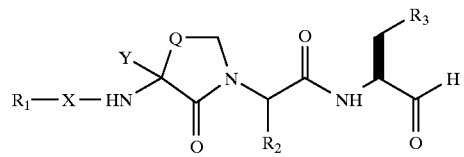

wherein:
(a) X is selected from the group consisting of —S(O)₂—, —N(R')—S(O)₂—, —(C=O)—, —OC(=O)—, —NH—C(=O)—, —P(O)(R")— and a direct link, wherein R' is hydrogen, alkyl of 1 to about 4 carbon atoms, aryl of about 6 to about 14 carbon atoms or aralkyl of about 6 to about 16 carbon atoms, and R" is NR', OR', R', or SR', with the proviso that R" is not NH, OH, H, or SH, and;
(b) R₁ is selected from the group consisting of:
 (1) alkyl of 1 to about 12 carbon atoms,
 (2) alkyl of 1 to about 3 carbon atoms substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons, (3) cyclic alkyl of 3 to about 15 carbon atoms, which optionally is substituted in the ring carbons with hydroxyl, amino, guanidino, amidino, or alkoxyl or alkyl each of which is 1 to about 3 carbons, (4) heterocycloalkyl of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, optionally substituted in the ring carbons with hydroxyl, alkoxyl or alkyl each of which is 1 to about 3 carbons, amino, guanidino, or amidino, (5) heterocyclo of 4 to about 10 ring atoms with the ring atoms selected from carbon and heteroatoms, wherein the heteroatoms are selected from the group consisting of oxygen, nitrogen, and $S(O)_i$, wherein i is 0, 1, or 2, optionally substituted in the ring carbons with hydroxyl, alkoxyl or alkyl each of which is 1 to about 3 carbons, amino, guanidino, or amidino, (6) alkenyl of about 3 to about 6 carbon atoms which is optionally substituted with cyclic alkyl of about 5 to about 8 carbon atoms, which optionally is substituted in the ring carbons with hydroxyl, amino, guanidino, amidino, or alkoxyl or alkyl each of which is 1 to about 3 carbons, (7) aryl of about 6 to about 14 carbon atoms which is optionally mono-, di- or tni-substituted with $Y_1$, $Y_2$, and/or $Y_3$, respectively, (8) heteroaryl of 5 to 14 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively, (9) aralkyl of about 7 to about 15 carbon atoms which is optionally mono-, di-, or tri-substituted in the aryl ring with $Y_1$, $Y_2$, and/or $Y_3$, respectively,

(10) heteroaralkyl of 6 to 11 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively,

(11) aralkenyl of about 8 to about 15 carbon atoms which is optionally mono-, di-, or tri-substituted in the aryl ring with $Y_1$, $Y_2$, and/or $Y_3$, respectively,

(12) heteroaralkenyl of 7 to 12 atoms with the ring atoms selected from carbon and heteroatoms, wherein the heteroatoms are selected from oxygen, nitrogen, and $S(O)_i$, wherein i is 0, 1, or 2, optionally mono-, di- or tri-substituted with $Y_1$, $Y_2$, and/or $Y_3$, respectively, (13)

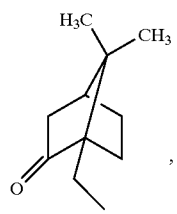

(14)

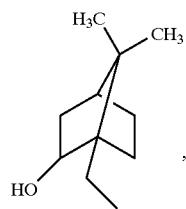

(15)

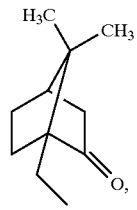

(16)

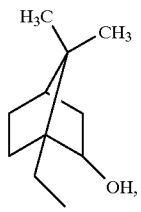

(17) perfluoroalkyl of 1 to about 12 carbon atoms,
(18) perfluoroaryl of about 6 to about 14 carbon atoms,
(19) perfluoroaralkyl of about 7 to about 15 carbon atoms,
(20) hydrogen, and
(21)

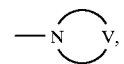

wherein

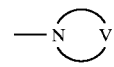

is a 5 to 7 member heterocycle of 3 to 6 ring carbon atoms, where V is —$CH_2$—, —O—, —S(=O)—, —$S(O)_2$— or —S—, wherein $Y_1$, $Y_2$, and $Y_3$ are (i) independently selected from the group consisting of hydrogen, halogen, cyano, tetrazolyl, amino, guanidino, amidino, methylamino, and methylguanidino, —$CF_3$, —$CF_2H$, —$CF_2CF_3$, —$CH(CF_3)_2$, —$C(OH)(CF_3)_2$, $OCF_3$, $OCF_2CF_3$, —$OC(O)NH_2$, —$OC(O)NHZ_1$, —$OC(O)NZ_1Z_2$, —$NHC(O)Z_1$, —$NHC(O)NH_2$, —$NHC(O)NZ_1$, —$NHC(O)NZ_1Z_2$, —$C(O)OH$, —$C(O)NH_2$, —$C(O)NHZ_1$, —$C(O)OZ_1$, —$P(O)_3H$, —$P(O)_3H_2$, —$P(O)_3(Z_1)_2$, —$S(O)_3H$, —$S(O)_mZ_1$, —$Z_1$, —$OZ_1$, —OH, —$NH_2$, —$NHZ_1$, and —$NZ_1Z_2$, wherein m is 0, 1 or 2, and $Z_1$ and $Z_2$ are independently selected from the group consisting of alkyl of 1 to about 12 carbon atoms, aryl of about 6 to about 14 carbon atoms, heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, or (ii) $Y_1$ and $Y_2$ are selected together to be —OC($Z_3$)($Z_4$)O, wherein $Z_3$ and $Z_4$ are independently selected from the group consisting of hydrogen, alkyl of 1 to about 12 carbon atoms, aryl of about 6 to about 14 carbon atoms heteroaryl of about 5 to about 14 atoms having 1 to about 9 carbon atoms, aralkyl of about 7 to about 15 carbon atoms, and heteroaralkyl of about 6 to about 11 atoms having about 3 to about 9 carbon atoms, (c) Q is —(CH$_2$)n—, wherein n is an integer from 1 to 4, or —(CH$_2$)$_q$R$_4$—, wherein q is 1 or 2, and R$_4$ is —S(O)$_p$—, O, —N(R$_5$)—, wherein p is 0, 1, or 2 and R$_5$ is selected from the group consisting of hydrogen, alkyl of 1 to 4 carbon atoms, and aryl of 1 to 4 carbon atoms;

(d) R$_2$ is selected from the group consisting of hydrogen, alkyl of 1 to 4 carbon atoms or alkenyl of 2 to 4 carbon atoms; and (e) R$_3$ is selected from the group consisting of

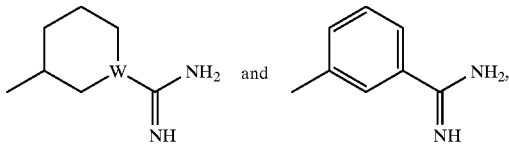

where W is nitrogen or carbon; and (f) Y is selected from the group of R$_1$ substituents, with the proviso that Y is not

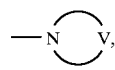

and pharmaceutically acceptable salts thereof.

2. A compound according to claim 1, wherein X is selected from the group consisting of a direct link, —SO$_2$—, —NH—S(O)$_2$—, and —N(R')—S(O)$_2$—.

3. A compound according to claim 2, wherein X is a direct link or —SO$_2$—.

4. A compound according to claim 1, wherein R$_1$ is selected from the group consisting of alkyl, aralkyl and aryl.

5. A compound according to claim 4, wherein R$_1$ is selected from the group consisting of substituted or unsubstituted benzyl, phenyl and naphthyl.

6. A compound according to claim 4, wherein the aryl is selected from the group consisting of —C(O)OH, —C(O)OZ$_1$, —CH$_3$, —OCH$_3$, and —CF$_3$.

7. A compound according to claim 4, wherein R$_1$ is aralkyl.

8. A compound according to claim 4, wherein R$_1$ is cyclohexyl or cyclohexylmethyl.

9. A compound according to claim 1, wherein Q is —(CH$_2$)$_2$— or —(CH$_2$)$_3$—.

10. A compound according to claim 1, wherein R$_2$ is hydrogen.

11. A compound according to claim 1, wherein R$_3$ is

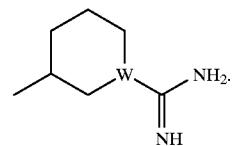

12. A compound according to claim 11, wherein W is nitrogen.

13. A compound according to claim 1, wherein Y is selected from the group consisting of (a) hydrogen, (b) phenyl—(CH$_2$)$_x$—, wherein x is an integer from 0 to 3, and the phenyl is optionally mono-, di-, or tri-substituted with with Y$_1$, Y$_2$, and/or Y$_3$, respectively, (c) heteroaryl—(CH$_2$)$_x$—, wherein x is an integer from 0 to 3, and the heteroaryl is optionally mono-, di-, or tri-substituted with Y$_1$, Y$_2$, and/or Y$_3$, respectively, (d) heterocycloalkyl—(CH$_2$)$_x$—, wherein x is an integer from 0 to 3, and the heterocycloalkyl is optionally substituted with hydroxyl, alkoxyl, or alkyl of 1 to about 3 carbons, (e) C$_5$ to C$_8$ cycloalkenyl, optionally mono-, di-, or tri-substituted with Z$_5$, Z$_6$, and/or Z$_7$, respectively, (f) C$_5$ to C$_8$ cycloalkyl, optionally mono-, di-, or tri-substituted with with Z$_5$, Z$_6$, and/or Z$_7$, respectively, wherein Z$_5$, Z$_6$, and/or Z$_7$ are independently selected from the group consisting of R$_6$, OR$_6$, and CO$_2$R$_6$, wherein R$_6$ is selected from the group consisting of hydrogen, methyl, alkyl of 1–3 carbon atoms.

14. A compound according to claim 13, wherein Y is aralkyl or cycloalkyl.

15. A compound according to claim 14, wherein Y is substituted or unsubstituted benzyl and 1-naphthylmethyl.

16. A compound according to claim 15, wherein the substitution is selected from the group consisting of —C(O)OH, —C(O)OZ$_1$, —CH$_3$, —OCH$_3$, and —CF$_3$.

17. A compound according to claim 15, wherein the cycloalkyl contains 5 to 8 ring carbons.

18. A compound according to claim 17, wherein the cycloalkyl is substituted with a substitution selected from the group consisting of —C(O)OH, —C(O)OZ$_1$, —CH$_3$, and —OCH$_3$.

19. A compound according to claim 1, wherein X is —S(O)$_2$—, R$_1$ is substituted or unsubstituted aralkyl, Q is —(CH$_2$)$_2$—, R$_2$ is hydrogen and R$_3$ is

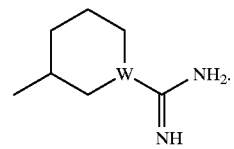

20. A compound according to claim 19, wherein W is nitrogen.

21. A compound according to claim 19, wherein R$_1$ is substituted or unsubstituted benzyl.

22. A compound according to claim 1, wherein X is —S(O)$_2$—, R$_1$ is substituted or unsubstituted aralkyl, Q is —(CH$_2$)$_3$—, R$_2$ is hydrogen and R$_3$ is

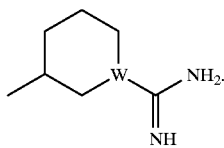

23. A compound according to claim 22, wherein W is nitrogen.

24. A compound according to claim 23, wherein $R_1$ is substituted or unsubstituted benzyl.

25. A compound according to claim 1 wherein X is —S(O)$_2$—.

26. A compound according to claim 25 wherein Q is —CH$_2$—.

27. A compound according to claim 25 wherein Q is —CH$_2$S(O)$_p$—.

28. A compound according to claim 25 wherein Q is —(CH$_2$)$_2$—.

29. A compound according to claim 25 wherein Q is —(CH$_2$)$_3$—.

30. A compound according to claim 28 wherein $R_1$ is aryl or aralkyl.

31. A compound according to claim 30 wherein $R_2$ is hydrogen.

32. A compound according to claim 31 wherein $Y_1$, $Y_2$, and/or $Y_3$ are independently selected from —C(O)OH, —C(O)O$Z_1$, —S(O)$_m$Z, and —S(O)$_3$H.

33. A compound according to claim 32 wherein $R_3$ is

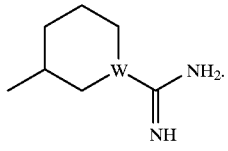

34. A compound according to claim 33 wherein W is nitrogen.

35. A compound according to claim 34 wherein $R_1$ is unsubstituted naphthyl, substituted naphthyl, unsubstituted benzyl or substituted benzyl.

36. A compound according to claim 35 wherein $R_1$ is benzyl.

37. A compound according to claim 10 wherein X is —S(O)$_2$—.

38. A compound according to claim 37 wherein $R_1$ is aryl or aralkyl.

39. A compound according to claim 38 wherein $R_3$ is

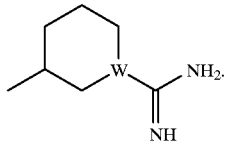

40. A compound according to claim 39 wherein W is nitrogen.

41. A compound according to claim 40 wherein Q is —(CH$_2$)$_2$— or —CH$_2$S(O)$_p$— wherein p is 0.

42. A compound according to claim 1 wherein Q is —(CH$_2$)$_2$—.

43. A compound according to claim 1 wherein X is —S(O)$_2$—, $R_1$ is aralkyl and $R_2$ is hydrogen.

44. A compound according to claim 43 wherein $R_3$ is

45. A compound according to claim 43 wherein $R_3$ is

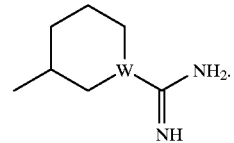

46. A compound according to claim 45 wherein W is nitrogen.

47. A compound according to claim 46 wherein $R_1$ is unsubstituted benzyl or substituted benzyl.

48. A compound according to claim 47 wherein $Y_1$, $Y_2$, and/or $Y_3$ are independently selected from —C(O)OH, —C(O)O$Z_1$, —S(O)$_m$Z, and —S(O)$_3$H.

49. A compound according to claim 48 wherein Q is —(CH$_2$)$_2$—.

50. A compound according to claim 47 wherein Q is —(CH$_2$)$_2$—.

51. A compound according to claim 46 wherein W is —(CH$_2$)$_2$—.

52. A compound according to claim 1 wherein $R_3$ is

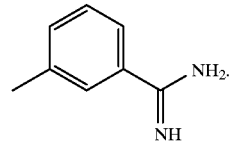

53. A compound according to claim 1 wherein $R_3$ is

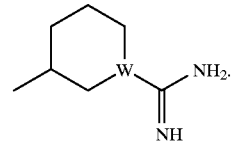

54. A compound according to claim 53 wherein W is nitrogen.

55. A compound according to claim 53 wherein W is carbon.

56. A compound selected from the group consisting of:
N-(benzylsulfonyl-norVal(cyclo)-Gly)-3-[3-piperidyl-(N-guanidino)]-L-alaninal,
N-(benzylsulfonyl-norLeu(cyclo)-Gly)-3-[3-piperidyl-(N-guanidino)]-L-alaninal,
N-(benzylsulfonyl-norVal(cyclo)-Gly-D,L-3-amidinophenylalaninal,
N-(benzylsulfonyl-norLeu(cyclo)-Gly-D,L-3-amidinophenylalaninal,
N-(norVal(cyclo)-Gly)-3-[3-piperidyl-(N-guanidino)]-L-alaninal,
N-(norLeu(cyclo)-Gly)-3-[3-piperidyl-(N-guanidino)]-L-alaninal, N-[(S)-3-N-phenylethylamino-2-oxo-1-piperidineacetyl]-3-[3-piperidyl-(N-guanidino)]-L-alaninal,
N-[(S)-3-N-phenylpropylamino-2-oxo-1-piperidineacetyl]-3-[3-piperidyl-(N-guanidino)]-L-alaninal,
N-[(S)-3-N-phenylethylamino-hexahydro-2-oxo-azepine-1-acetyl]-3-[3-piperidyl-(N-guanidino)]-L-alaninal,
N-(D, L-a-benzyl-norVal(cyclo)Gly)-3-[3-piperidyl-(N-guanidino)]-L-alaninal,
N-(D, L-a-benzyl-norLeu(cyclo)Gly)-3-[3-piperidyl-(N-guanidino)]-L-alaninal,
N-(1-naphthyl-$SO_2$-norVal(cyclo)-Gly)-3-[3-piperidyl-(N-guanidino)]-L-alaninal,
N-(2-naphthyl-$SO_2$-norVal(cyclo)-Gly)-3-[3-piperidyl-(N-guanidino)]-L-alaninal,
N-(1-naphthylmethyl-$SO_2$-norVal(cyclo)-Gly)-3-[3-piperidyl-(N-guanidino)]-L-alaninal,
N-(2-naphthylmethyl-$SO_2$-norVal(cyclo)-Gly)-3-[3-piperidyl-(N-guanidino)]-L-alaninal,
N-(phenyl-$SO_2$-norLeu(cyclo)Gly)-3-[3-piperidyl-(N-guanidino)]-L-alaninal,
N-(1-naphthyl-$SO_2$-norLeu(cyclo)-Gly)-3-[3-piperidyl-(N-guanidino)]-L-alaninal,
N-(2-naphthyl-$SO_2$-norLeu(cyclo)-Gly)-3-[3-piperidyl-(N-guanidino)]-L-alaninal,
N-(1-naphthylmethyl-$SO_2$-norLeu(cyclo)-Gly)-3-[3-piperidyl-(N-guanidino)]-L-alaninal,
N-(2-naphthylmethyl-$SO_2$-norLeu(cyclo)-Gly)-3-[3-piperidyl-(N-guanidino)]-L-alaninal,
N-(2-carbomethoxyphenyl-$SO_2$-norLeu(cyclo)-Gly)-3-[3-piperidyl-(N-guanidino)]-L-alaninal,
N-(2-carbomethoxybenzyl-$SO_2$-norLeu(cyclo)-Gly)-3-[3-piperidyl-(N-guanidino)]-L-alaninal,
N-(2-trifluoromethylphenyl-$SO_2$-norLeu(cyclo)-Gly)-3-[3-piperidyl-(N-guanidino)]-L-alaninal,
N-(2-trifluoromethylbenzyl-$SO_2$-norLeu(cyclo)-Gly)-3-[3-piperidyl-(N-guanidino)]-L-alaninal,
N-(cyclohexylmethyl-$SO_2$-norLeu(cyclo)-Gly)-3-[3-piperidyl-(N-guanidino)]-L-alaninal,
N-(cyclohexylmethyl-$SO_2$-norVal(cyclo)-Gly)-3-[3-piperidyl-(N-guanidino)]-L-alaninal,
N-(cyclohexylamino-$SO_2$-norLeu(cyclo)-Gly)-3-[3-piperidyl-(N-guanidino)]-L-alaninal,
N-(2-thiophenemethyl-$SO_2$-norLeu(cyclo)-Gly)-3-[3-piperidyl-(N-guanidino)]-L-alaninal),
N-(phenylamino-$SO_2$-norVal(cyclo)-Gly)-D,L-3-amidinophenylalaninal,
N-(phenylamino-$SO_2$-norLeu(cyclo)-Gly)-3-[3-piperidyl-(N-guanidino)]-L-alaninal,
N-(2-carbomethoxyphenylamino-$SO_2$-norLeu(cyclo)-Gly)-D,L-3-amidinophenylalaninal,
N-(3-carbomethoxybenzyl-$SO_2$-norLeu(cyclo)-Gly)-3-[3-piperidyl-(N-guanidino)]-L-alaninal,
N-(3-carbomethoxybenzyl-$SO_2$-norVal(cyclo)-Gly)-3-[3-piperidyl-(N-guanidino)]-L-alaninal),
N-(3-trifluoromethylbenzyl-$SO_2$-norVal(cyclo)-Gly)-3-[3-piperidyl-(N-guanidino)]-L-alaninal,
N-(3-trifluoromethylbenzyl-$SO_2$-norLeu(cyclo)-Gly)-3-[3-piperidyl-(N-guanidino)]-L-alaninal,
N-(2-methylbenzyl-$SO_2$-norLeu(cyclo)-Gly)-D, L-3-amidinophenylalaninal,
N-(2-methylbenzyl-$SO_2$-norLeu(cyclo)-Gly)-3-[3-piperidyl-(N-guanidino)]-L-alaninal,
N-(3-methylbenzyl-$SO_2$-norLeu(cyclo)-Gly)-3-[3-piperidyl-(N-guanidino)]-L-alaninal,
N-(3-methylbenzyl-$SO_2$-norVal(cyclo)-Gly)-3-[3-piperidyl-(N-guanidino)]-L-alaninal,
N-(3-methoxybenzyl-$SO_2$-norLeu(cyclo)-Gly)-3-[3-piperidyl-(N-guanidino)]-L-alaninal,
N-(3-methoxybenzyl-$SO_2$-norVal(cyclo)-Gly)-3-[3-piperidyl-(N-guanidino)]-L-alaninal,
N-(3-methoxybenzyl-$SO_2$-norVal(cyclo)-Gly)-D, L-3-amidinophenylalaninal,
N-(2-chlorobenzyl-$SO_2$-norLeu(cyclo)-Gly)-3-[3-piperidyl-(N-guanidino)]-L-alaninal,
N-(3-chlorobenzyl-$SO_2$-norLeu(cyclo)-Gly)-3-[3-piperidyl-(N-guanidino)]-L-alaninal,
N-(3-chlorobenzyl-$SO_2$-norVal(cyclo)-Gly)-D, L-3-amidinophenylalaninal,
N-(2-methyl-5-fluorobenzyl-$SO_2$-norLeu(cyclo)-Gly)-3-[3-piperidyl-(N-guanidino)]-L-alaninal,
N-(2-methyl-5-fluorobenzyl-$SO_2$-norLeu(cyclo)-Gly)-D, L-3-amidinophenylalaninal,
N-(2-methyl-5-fluorobenzyl-$SO_2$-norVal(cyclo)-Gly)-3-[3-piperidyl-(N-guanidino)]-L-alaninal,
N-(2-methyl-5-methoxybenzyl-$SO_2$-norLeu(cyclo)-Gly)-3-[3-piperidyl-(N-guanidino)]-L-alaninal,
N-(2-methyl-5-methoxybenzyl-$SO_2$-norLeu(cyclo)-Gly)-D, L-3-amidinophenylalaninal,
N-(Benzyl-PO-(OEt)-norLeu(cyclo)-Gly)-3-[3-piperidyl-(N-guanidino)]-L-alaninal,
N-(Benzyl-PO-(Me)-norLeu(cyclo)-Gly)-3-[3-piperidyl-(N-guanidino)]-L-alaninal),
N-(Benzyl-PO-(NHMe)-norLeu(cyclo)-Gly)-3-[3-piperidyl-(N-guanidino)]-L-alaninal,
N-(Benzyl-PO-(OEt)-norLeu(cyclo)-Gly)-D, L-3-amidinophenylalaninal,
N-(Benzyl-PO-(Me)-norVal(cyclo)-Gly)-3-[3-piperidyl-(N-guanidino)]-L-alaninal,
N-(Benzyl-PO-(NHMe)-norVal(cyclo)-Gly)-D,L-3-amidinophenylalaninal,
N-(Benzyl-$SO_2$-homoala(cyclo)-Gly)-3-[3-piperidyl-(N-guanidino)]-L-alaninal, and
N-(Benzyl-$SO_2$-homoala(cyclo)-Gly)-D,L-3-amidinophenylalaninal.

* * * * *